(12) United States Patent
Li et al.

(10) Patent No.: US 8,921,563 B2
(45) Date of Patent: Dec. 30, 2014

(54) 1-[(4-HYDROXYPIPERIDIN-4-YL)METHYL] PYRIDIN-2(1H)-ONE DERIVATIVES, PREPARATION METHODS AND USES THEREOF

(75) Inventors: Yunfeng Li, Beijing (CN); Rifang Yang, Beijing (CN); Youzhi Zhang, Beijing (CN); Yongzhen Li, Beijing (CN); Zengliang Jin, Beijing (CN); Peng Li, Beijing (CN); Li Yuan, Beijing (CN); Liuhong Yun, Beijing (CN); Nan Zhao, Beijing (CN); Cheng Zhang, Beijing (CN); Xiaodan Xu, Beijing (CN); Rusheng Zhao, Beijing (CN); Hongxia Chen, Beijing (CN); Rui Xue, Beijing (CN); Juanjuan Qin, Beijing (CN); Zhenzhen Wang, Beijing (CN); Jiazhi Yao, Beijing (CN)

(73) Assignee: Institue of Pharmacology and Toxicology Academy of Military Medical Sciences P.L.A., China, Beijing (CN)

( * ) Notice: Subject to any disclaimer, the term of this patent is extended or adjusted under 35 U.S.C. 154(b) by 0 days.

(21) Appl. No.: 13/697,857

(22) PCT Filed: Apr. 8, 2011

(86) PCT No.: PCT/CN2011/000612
§ 371 (c)(1),
(2), (4) Date: Dec. 21, 2012

(87) PCT Pub. No.: WO2011/140817
PCT Pub. Date: Nov. 17, 2011

(65) Prior Publication Data
US 2013/0231369 A1  Sep. 5, 2013

(30) Foreign Application Priority Data

May 14, 2010 (CN) .......................... 2010 1 0172483
Sep. 25, 2010 (CN) .......................... 2010 1 0290350

(51) Int. Cl.
*A61K 31/445* (2006.01)
*A61K 31/505* (2006.01)
*C07D 211/68* (2006.01)
*C07D 239/02* (2006.01)
*C07D 401/06* (2006.01)

(52) U.S. Cl.
CPC .................................... C07D 401/06 (2013.01)
USPC ............ 546/194; 544/315; 514/269; 514/318

(58) Field of Classification Search
None
See application file for complete search history.

(56) References Cited

FOREIGN PATENT DOCUMENTS

| JP | 10503768 A | 4/1998 |
|---|---|---|
| JP | 2005515995 A | 6/2005 |
| JP | 2009529573 A | 8/2009 |
| WO | WO 03/047577 A2 | 6/2003 |

OTHER PUBLICATIONS

CAPLUS 2011:183260.*
Extended European Search Report dated Nov. 26, 2013.
Morris Fishman, et al., "Studies in alkylation. I. Synthesis and reactions of spiro[oxirane-2,4-piperdines]," Journal of Heterocyclic Chemistry, vol. 5, No. 4, Aug. 1, 1968, pp. 467-469.
Kai, et al., "Antidepressant-like effect of a novel compound YL-0919," Guoji Yaoxue Yanjiu Zazhi, vol. 37, No. 5, Oct. 1, 2010, pp. 366-371.
David P. Rotella ed—Chad E Beyer, et al., "Chapter 7: Medicinal chemistry challenges in the design of next generation antidepressants," May 1, 2010, Next Generation Antidepressants: Moving Beyond Monoamines to Discover Novel Treatment Strategies for Mood Disorders, Cambridge University Press, US, pp. 102-118.
Enza Lacivita, et al., "5-HT1A Receptor, an Old Target for New Therapeutic Agents," Current Topics in Medicinal Chemistry, vol. 8, No. 12, Aug. 1, 2008, pp. 1024-1034.

* cited by examiner

*Primary Examiner* — Heidi Reese
(74) *Attorney, Agent, or Firm* — Brinks Gilson & Lione

(57) ABSTRACT

Provided are N-[(4-hydroxypiperidin-4-yl)methyl]pyridin-2 (1H)-one derivatives represented by formula I, stereoisomers, pharmaceutically acceptable salts or solvates thereof.

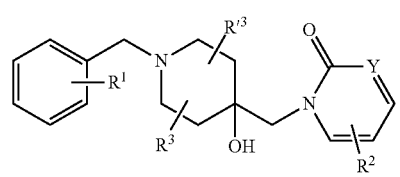

The above compounds have the dual activities of 5-hydroxytryptamine 1A receptor ligand and selective serotonin reuptake inhibitor. The preparation methods of the above compounds, the uses of these compounds for the prevention or treatment of nervous system diseases related to 5-hydroxytryptamine system dysfunction and the pharmaceutical compositions containing these compounds are also provided.

14 Claims, 2 Drawing Sheets

US 8,921,563 B2

1-[(4-HYDROXYPIPERIDIN-4-YL)METHYL] PYRIDIN-2(1H)-ONE DERIVATIVES, PREPARATION METHODS AND USES THEREOF

CROSS-REFERENCE TO RELATED APPLICATIONS

The present application is a §371 national stage application of PCT International Application No. PCT/CN2011/000612, filed Apr. 8, 2011, which application claims a right of priority to Chinese Patent Application No. 201010172483.5, filed May 14, 2010, and Chinese Application No. 2010/10290350.8, filed Sep. 25, 2010, both of which are incorporated herein by reference in their entirety.

TECHNICAL FIELD

The present invention belongs to the field of medicine and chemical industry and relates to a N-[(4-hydroxypiperidin-4-yl)methyl]pyridin-2(1H)-one derivative, a stereoisomer, pharmaceutically acceptable salt and solvate thereof having dual activities of 5-hydroxytryptamine 1A (5-$HT_{1A}$) receptor ligand and selective serotonin reuptake inhibitor (SSRI). The present invention further relates to preparation methods of the compounds, the uses thereof for the prevention or treatment of nervous system diseases associated with 5-HT system dysfunction, such as depression, anxiety, cognitive deficit, mania, schizophrenia, Parkinson's disease, pain, drug dependence (or drug addiction) and relapse, various kinds of mental stress disorder and fear, anorexia, sleep disorder, sexual dysfunction, gastrointestinal dysfunction (e.g., nausea, vomiting, etc.), respiratory depression, kidney dysfunction, or endocrine and immune dysfunction, the uses thereof as tool drug for studying 5-HT functions and diseases associated with 5-HT dysfunctions, and pharmaceutical compositions comprising the compounds.

BACKGROUND ART

5-Hydroxytryptamine (5-HT), also called as serotonin, is either an important monoamine neurotransmitter, or a vasoactive substance, 5-HT is widely distributed in central nervous system (CNS), participates the control and regulation of almost all physiological and behavior functions in human body, including feelings, cognitions, sensations, neurotrophy, appetite, endocrine function, gastrointestinal tract function, motion function, sex behavior and sleep. The studying of various 5-HT receptors (5-HTR) facilitates the interpretation of various physiological and pathological mechanisms of nerve and mental disorders, as well as the formulation of corresponding therapeutic strategy. At present, human 5-HTR has at least 7 types (5-$HT_1$R to 5-$HT_7$R), these 7 kinds of receptors can be further divided into several subtypes. Among numerous subtypes of 5-HTR, the research of 5-$HT_{1A}$R is the deepest and widest one, and the development of prospect of ligands thereof is very promising.

5-$HT_{1A}$R is an important regulation factor for 5-HT system neural transmission. When neural impulse reaches nerve terminal, presynaptic membrane vesicles release neurotransmitter 5-HT to synaptic cleft. After acting with 5-HTR of synaptic membrane, most of the 5-HT is subjected to selective serotonin reuptake (SSR) and enters back into presynaptic membrane, in which a part thereof enters again into synaptic vesicles for storage, another part is degraded by monoamine oxidase to terminate activity thereof 5-$HT_{1A}$R signal transductions are all performed by coupling to G protein, inhibiting adenylate cyclase activity, therefor decreasing the synthesis of second messenger cyclic adenosine monophosphate (cAMP), activating potassium ion channels, resulting hyperpolarization of membrane, forming inhibitory post synaptic potential, and then initiating cytological effects.

In addition, 5-$HT_{1A}$R further participates the regulation of hypothalamic-pituitary-adrenal axis (HPA) which has important functions in stress response. Many researches confirm that 5-$HT_{1A}$R plays very important role in many functional activity of central nervous system, and closely relates to anxiety, depression, schizophrenia, pain, cognition, eating behavior, sex activity, Alzheimer disorder and sleep-waking cycle, etc.

Hence, it has important significance to develop a novel selective regulation ligand of 5-$HT_{1A}$R (5-$HT_{1A}$RL), for example, the well-known 5-$HT_{1A}$R partial agonists (e.g., buspirone, etc.) are important anxiolytic drug widely used in clinic, meanwhile, they also have antidepressant activity.

Selective serotonin reuptake inhibitors (SSRIs) selectively target on 5-HT transporter, they are current first-line antidepressants and anxiolytics in clinic, such as sertraline, fluoxetine and paroxetine, etc.

Many experimental and clinical data show that the use of combination of 5-$HT_{1A}$RL drug and selective serotonin reuptake inhibitor (SSRIs) drug can shorten onset time, and enhance the therapeutic efficiency. The design and synthesis of novel ligands having dual activities of 5-$HT_{1A}$RL and SSRI, and proceeding related pharmacological study thereof will very helpful in the development of novel, fewer side-effects and faster onset neuropsychoactive drugs including antidepressants, anxiolytics and cognition enhancer ect.

The early data found that aryl piperazine compound Vilazodone (EMD 68843) is a dual 5-$HT_{1A}$R partial agonist and SSRIs, which exhibits well antidepressant effect, and is in phase III clinical research, but its clinical therapeutic effects are still not satisfied (M E Page, et al. *J Pharmacol Exp Ther*, 2002, 302: 1220; M J Milan. *Neurotherapeutics*, 2009, 6: 53). SB-649915 has 5-$HT_{1A/1B}$R antagonistic effect and inhibit 5-HT reuptake, and it exert faster anxiolytic effects (M J Milan. *Neurotherapeutics*, 2009, 6: 53). At present, it is mainly based on the dual 5-HTRL and SSRI action mechanism to attempt to incorporate the pharmacophores of the both into one molecule, for example, a substituted indole ring or benzothiophene ring having activity to 5-HT transporter can be organically linked to a pharmacophore (e.g., arylpiperazine or tetrahydroisoquinolin) having function to 5-$HT_{1A}$R, to achieve dual functions of using the same one small molecule to regulate 5-$HT_{1A}$R and inhibit 5-HT transporter at the same time, so as to bring about effects of quick onset in anti-depression and antianxiety (L I Peng, YANG Rifang, L I Jin, YUN Liuhong. Advances in research of 5-hydroxytryptamine (5-HT)$_{1A}$ receptor ligand. Chinese Journal of Medicinal Chemistry, 2008, 18(3), 228-238).

At present, it is still in need to find novel compounds having dual activities to 5-$HT_{1A}$RL and SSRI for clinical application.

CONTENTS OF THE INVENTION

The inventors have found via intensive study that a novel compound of Formula I has dual effects on 5-HTRL and SSRI, and its structure has not been reported so far. The inventors have found a compound of Formula I having dual effects on 5-HTRL and SSRI, and the compound can be used for the prevention or treatment of diseases such as depression, anxiety, cognitive deficit, mania, schizophrenia, Parkinson's disease, pain, drug dependence (or drug addiction) and relapse, various kinds of mental stress disorder and fear, anorexia, sleep disorder, sexual dysfunction, gastrointestinal dysfunction (e.g., nausea, vomiting, etc.), respiratory depression, kidney dysfunction, or endocrine and immune dysfunction. The study results show that the compound of Formula I has effects of regulating functions of $5\text{-}HT_{1A}R$ and 5-HT transporter. Further synthesis and studies show that a pharmaceutically acceptable salt formed by reacting the derivative of the present invention with a suitable inorganic acid or organic acid or with an inorganic base or organic base also has effects of regulating functions of $5\text{-}HT_{1A}R$ and 5-HT transporter. The present invention is fulfilled on the basis of the above findings.

BRIEF DESCRIPTION OF THE INVENTION

The first aspect of the present invention relates to a compound of Formula I, a tautomer thereof, a racemate or optical isomer thereof, a pharmaceutically acceptable salt or a solvate thereof having function of regulating 5-HT system,

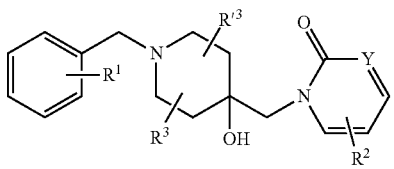

I wherein:
$R^1$, $R^2$ are H, halogen (F, Cl, Br, I), alkyl, substituted hydrocarbyl, alkenyl, substituted alkenyl, phenyl, substituted phenyl, heteroaryl, substituted heteroaryl, $C_1\text{-}C_6$ alkoxy, $C_5\text{-}C_{10}$ aryloxy, substituted aryloxy, $C_1\text{-}C_6$ alkylamino, $C_5\text{-}C_{10}$ arylamino, substituted arylamino, di-($C_1\text{-}C_6$ alkyl)amino, di-($C_5\text{-}C_{10}$ aryl)amino, di-(substituted aryl)amino, $C_{1\text{-}10}$ hydrocarbylacyloxy, $C_{6\text{-}10}$ arylacyloxy, $C_{1\text{-}10}$ hydrocarbylamido, $C_{6\text{-}10}$ arylamido, carboxy, $C_{1\text{-}10}$ hydrocarbyloxyformyl, $C_{6\text{-}10}$ aryloxyformyl, carbamoyl, $C_{1\text{-}10}$ hydrocarbylaminoformyl, or $C_{6\text{-}10}$ arylaminoformyl; wherein the heteroaryl ring is a monocyclic or fused cyclic aromatic hydrocarbyl having 1-3 heteroatoms selected from the group consisting of N, O or S, the substituent of each substituted group is selected from the group consisting of halogen, hydroxy, cyano, nitro, $C_{1\text{-}6}$ alkyl, $C_{1\text{-}6}$ alkoxy, $C_{1\text{-}6}$ alkylthio, mono-, di- or tri-halogenated $C_{1\text{-}6}$ alkyl, amino, $C_{1\text{-}6}$ alkylamino, $C_{1\text{-}10}$ hydrocarbylacyloxy, $C_{1\text{-}10}$ hydrocarbylamido, $C_{6\text{-}10}$ arylacyloxy or $C_{6\text{-}10}$ arylamido;

$R^1$, $R^2$ can be same or different, wherein $R^1$ can represent 1-3 substituents which can be at o-, m- or p-position of benzene ring; $R^2$ can represent 1-3 substituents (when Y is CH, $R^2$ represent at most 3 substituents which can be at 3-, 4-, 5- or 6-position; when Y is N, $R^2$ represent at most 2 substituents which can be at 4-, 5- or 6-position of heterocyclic ring);

$R^3$, $R^{i3}$ independently are H, alkyl, substituted hydrocarbyl, alkenyl, substituted alkenyl, $C_1\text{-}C_6$ alkoxy, $C_5\text{-}C_{10}$ aryloxy, substituted aryloxy, $C_1\text{-}C_6$ alkylamino, $C_5\text{-}C_{10}$ arylamino, substituted arylamino, di-($C_1\text{-}C_6$ alkyl)amino, $C_{1\text{-}10}$ hydrocarbylacyloxy, $C_{6\text{-}10}$ arylacyloxy, $C_{1\text{-}10}$ hydrocarbylamido, $C_{6\text{-}10}$ arylamido, $C_{1\text{-}10}$ hydrocarbyloxyformyl, $C_{6\text{-}10}$ aryloxyformyl, carbamoyl, $C_{1\text{-}10}$ hydrocarbylaminoformyl, or $C_{6\text{-}10}$ arylaminoformyl; wherein the heteroaryl ring is a monocyclic or fused cyclic aromatic hydrocarbyl having 1-3 heteroatoms selected from the group consisting of N, O or S, the substituent of each substituted group is selected from the group consisting of halogen, hydroxy, cyano, nitro, $C_{1\text{-}6}$ alkyl, $C_{1\text{-}6}$ alkoxy, $C_{1\text{-}6}$ alkylthio, mono-, di- or tri-halogenated $C_{1\text{-}6}$ alkyl, amino, $C_{1\text{-}6}$ alkylamino, $C_{1\text{-}10}$ hydrocarbylacyloxy, $C_{1\text{-}10}$ hydrocarbylamido, $C_{6\text{-}10}$ arylacyloxy or $C_{6\text{-}10}$ arylamido;

Y is CH or N.

Specifically, the first aspect of the present invention provides a compound of Formula I, a tautomer thereof, a racemate or optical isomer thereof, a pharmaceutically acceptable salt or a solvate thereof,

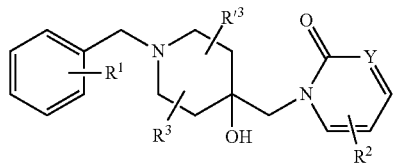

I wherein:
$R^1$, $R^2$ each independently is H, halogen (F, Cl, Br, I), $C_1\text{-}C_6$ alkyl, substituted $C_1\text{-}C_6$ alkyl, $C_1\text{-}C_6$ alkenyl, substituted $C_1\text{-}C_6$ alkenyl, phenyl, substituted phenyl, heteroaryl, substituted heteroaryl, $C_1\text{-}C_6$ alkoxy, $C_5\text{-}C_{10}$ aryloxy, substituted $C_5\text{-}C_{10}$ aryloxy, $C_1\text{-}C_6$ alkylamino, $C_5\text{-}C_{10}$ arylamino, substituted $C_5\text{-}C_{10}$ arylamino, di-($C_1\text{-}C_6$ alkyl)amino, di-($C_5\text{-}C_{10}$ aryl)amino, di-(substituted $C_5\text{-}C_{10}$ aryl)amino, $C_{1\text{-}10}$ hydrocarbylacyloxy, $C_{6\text{-}10}$ arylacyloxy, $C_{1\text{-}10}$ hydrocarbylamido, $C_{6\text{-}10}$ arylamido, carboxy, $C_{1\text{-}10}$ hydrocarbyloxyformyl, $C_{6\text{-}10}$ aryloxyformyl, carbamoyl, $C_{1\text{-}10}$ hydrocarbylaminoformyl, or $C_{6\text{-}10}$ arylaminoformyl; wherein the heteroaryl ring is a monocyclic or fused cyclic aromatic hydrocarbyl having 1-3 heteroatoms selected from the group consisting of N, O or S, the substituent of each substituted group is selected from the group consisting of halogen, hydroxy, cyano, nitro, $C_{1\text{-}6}$ alkyl, $C_{1\text{-}6}$ alkoxy, $C_{1\text{-}6}$ alkylthio, mono-, di- or tri-halogenated $C_{1\text{-}6}$ alkyl, amino, $C_{1\text{-}6}$ alkylamino, $C_{1\text{-}10}$ hydrocarbylacyloxy, $C_{1\text{-}10}$ hydrocarbylamido, $C_{6\text{-}10}$ arylacyloxy or $C_{6\text{-}10}$ arylamido;

$R^1$ and $R^2$ can be same or different, wherein $R^1$ can represent 1-3 substituents which can be at o-, m- or p-position of benzene ring; $R^2$ can represent 1-3 substituents (when Y is CH, $R^2$ represent at most 3 substituents which can be at 3-, 4-, 5- or 6-position; when Y is N, $R^2$ represent at most 2 substituents which can be at 4-, 5- or 6-position of heterocyclic ring);

$R^3$, $R^{i3}$ independently are H, alkyl, substituted hydrocarbyl, alkenyl, substituted alkenyl, $C_1\text{-}C_6$ alkoxy, $C_5\text{-}C_{10}$ aryloxy, substituted aryloxy, $C_1\text{-}C_6$ alkylamino, $C_5\text{-}C_{10}$ arylamino, substituted arylamino, di-($C_1\text{-}C_6$ alkyl)amino, $C_{1\text{-}10}$ hydrocarbylacyloxy, $C_{6\text{-}10}$ arylacyloxy, $C_{1\text{-}10}$ hydrocarbylamido, $C_{6\text{-}10}$ arylamido, $C_{1\text{-}10}$ hydrocarbyloxyformyl, $C_{6\text{-}10}$ aryloxyformyl, carbamoyl, $C_{1\text{-}10}$ hydrocarbylaminoformyl, or $C_{6\text{-}10}$ arylaminoformyl; wherein the heteroaryl ring is a monocyclic or fused cyclic aromatic hydrocarbyl having 1-3 heteroatoms selected from the group consisting of N, O or S, the substituent of each substituted group is selected from the group consisting of halogen, hydroxy, cyano, nitro, $C_{1\text{-}6}$ alkyl, $C_{1\text{-}6}$ alkoxy, $C_{1\text{-}6}$ alkylthio, mono-, di- or tri-halogenated $C_{1\text{-}6}$ alkyl, amino, $C_{1\text{-}6}$ alkylamino, $C_{1\text{-}10}$ hydrocarbylacyloxy, $C_{1\text{-}10}$ hydrocarbylamido, $C_{6\text{-}10}$ arylacyloxy or $C_{6\text{-}10}$ arylamido;

Y is CH or N.

The compound of Formula I according to the first aspect of the present invention, a tautomer thereof, a racemate or optical isomer thereof, a pharmaceutically acceptable salt or a solvate thereof, wherein Y is CH. The compound of Formula I according to the first aspect of the present invention, a tautomer thereof, a racemate or optical isomer thereof, a pharmaceutically acceptable salt or a solvate thereof, wherein Y is N.

The compound of Formula I according to the first aspect of the present invention, a tautomer thereof, a racemate or optical isomer thereof, a pharmaceutically acceptable salt or a solvate thereof, wherein $R^1$, $R^2$, $R^3$, $R'^3$ each independently is H, halogen (F, Cl, Br, I), $C_1$-$C_6$ alkyl, substituted $C_1$-$C_6$ alkyl, $C_1$-$C_6$ alkenyl, substituted $C_1$-$C_6$ alkenyl, phenyl, substituted phenyl, heteroaryl, substituted heteroaryl, $C_1$-$C_6$ alkoxy, $C_5$-$C_{10}$ aryloxy, substituted $C_5$-$C_{10}$ aryloxy, $C_1$-$C_6$ alkylamino, $C_5$-$C_{10}$ arylamino, substituted arylamino, di-($C_1$-$C_6$ alkyl)amino, $C_{1-10}$ hydrocarbylacyloxy, $C_{6-10}$ arylacyloxy, $C_{1-10}$ hydrocarbylamido, $C_{6-10}$ arylamido, carboxy, $C_{1-10}$ hydrocarbyloxyformyl, $C_{6-10}$ aryloxyformyl, carbamoyl, $C_{1-10}$ hydrocarbylaminoformyl, or $C_{6-10}$ arylaminoformyl; wherein the heteroaryl ring is a monocyclic or fused cyclic aromatic hydrocarbyl having 1-3 heteroatoms selected from the group consisting of N, O or S, the substituent of each substituted group is selected from the group consisting of halogen, hydroxy, cyano, nitro, $C_{1-6}$ alkyl, $C_{1-6}$ alkoxy, $C_{1-6}$ alkylthio, mono-, di- or tri-halogenated $C_{1-6}$ alkyl, amino, $C_{1-6}$ alkylamino, $C_{1-10}$ hydrocarbylacyloxy, $C_{1-10}$ hydrocarbylamido, $C_{6-10}$ arylacyloxy or $C_{6-10}$ arylamido; wherein $R^1$ can represent 1-3 substituents which can be at o-, m- or p-position of benzene ring; $R^2$ can have 1-2 substituents, can be at 3-, 4- or 5-position of the hetero ring. In one embodiment of the first aspect of the present invention, $R^1$, $R^2$, $R^3$, $R'^3$ each independently is H, halogen (F, Cl, Br, I), $C_1$-$C_6$ alkyl, substituted $C_1$-$C_6$ alkyl, or $C_1$-$C_6$ alkoxy; wherein the heteroaryl ring is a monocyclic or fused cyclic aromatic hydrocarbyl having 1-3 heteroatoms selected from the group consisting of N, O or S, the substituent of each substituted group is selected from the group consisting of halogen, hydroxy, cyano, nitro, $C_{1-6}$ alkyl, $C_{1-6}$ alkoxy, $C_{1-6}$ alkylthio, mono-, di- or tri-halogenated $C_{1-6}$ alkyl, amino, $C_{1-6}$ alkylamino, $C_{1-10}$ hydrocarbylacyloxy, $C_{1-10}$ hydrocarbylamido, $C_{6-10}$ arylacyloxy or $C_{6-10}$ arylamido. In one embodiment of the first aspect of the present invention, $R^1$, $R^2$, $R^3$, $R'^3$ each independently is H, F, Cl, Br, I, $C_1$-$C_6$ alkyl, $C_1$-$C_3$ alkoxyethyl, or $C_1$-$C_6$ alkoxy. In one embodiment of the first aspect of the present invention, $R^1$, $R^2$, $R^3$, $R'^3$ each independently is H, F, Cl, Br, $C_1$-$C_4$ alkyl, or $C_1$-$C_4$ alkoxy. In one embodiment of the first aspect of the present invention, $R^1$, $R^2$, $R^3$, $R'^3$ each independently is H, F, Cl, Br, methyl, ethyl, methoxyethyl, methoxy, or ethoxy.

The compound of Formula I according to the first aspect of the present invention, a tautomer thereof, a racemate or optical isomer thereof, a pharmaceutically acceptable salt or a solvate thereof, wherein Y is CH. In one embodiment of the first aspect of the present invention, Y is N. In one embodiment of the first aspect of the present invention, Y is CH.

The compound of Formula I according to the first aspect of the present invention, a tautomer thereof, a racemate or optical isomer thereof, a pharmaceutically acceptable salt or a solvate thereof, wherein $R^1$ represents H, 2-F, 4-F, 2,3-difluoro, 2,4-difluoro, 2,5-fluoro or 2,6-difluoro; $R^2$ is H, methyl, or methoxy; $R^3$ are H, methyl or methoxy. According to the present invention, for example, when the $R^1$ is 2,6-difluoro, it refers to that the left benzene ring of Formula I structure is substituted with fluorine atoms at 2- and 6-position, and other similar descriptions have similar meanings as well.

In one embodiment of the first aspect of the present invention, a compound of Formula I or a tautomer thereof, race mate, optical isomer, pharmaceutically acceptable salt or a solvate thereof is provided,

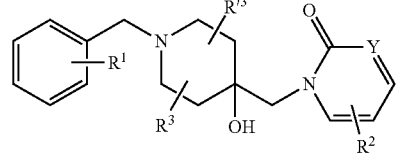

wherein:

$R^1$ represents H or represents 1-3 (e.g., 1-2) substituents selected from halogen (e.g., F, Cl, Br, I);

$R^2$ represents H or represents 1-3 (e.g., 1-2) substituents selected from the group consisting of: halogen (e.g., F, Cl, Br, I), $C_{1-6}$ alkyl (e.g., $C_{1-4}$ alkyl or $C_{1-3}$ alkyl, for example, methyl, ethyl, n-propyl, iso-butyl, n-butyl, tert-butyl);

$R^3$ and $R'^3$ each are H;

Y is CH.

The compound of Formula I according to the first aspect of the present invention, which is selected from the group consisting of:

1-[(1-benzyl-4-hydroxypiperidin-4-yl)-methyl]-pyridin-2(1H)-one;

1-{[1-(2-fluorobenzyl)-4-hydroxypiperidin-4-yl]-methyl}-pyridin-2(1H)-one;

1-{[1-(4-fluorobenzyl)-4-hydroxypiperidin-4-yl]-methyl}-pyridin-2(1H)-one;

1-{[1-(2,4-difluorobenzyl)-4-hydroxypiperidin-4-yl]-methyl}-pyridin-2(1H)-one;

5-bromo-1-[(1-benzyl-4-hydroxypiperidin-4-yl)-methyl]-pyridin-2(1H)-one;

5-bromo-1-{[1-(2-fluorobenzyl)-4-hydroxypiperidin-4-yl]-methyl}-pyridin-2(1H)-one;

5-bromo-1-{[1-(4-fluorobenzyl)-4-hydroxypiperidin-4-yl]-methyl}-pyridin-2(1H)-one;

5-bromo-1-{[1-(2,4-difluorobenzyl)-4-hydroxypiperidin-4-yl]-methyl}-pyridin-2(1H)-one;

1-[(1-benzyl-4-hydroxypiperidin-4-yl)-methyl]-4-methyl-pyridin-2(1H)-one;

1-{[1-(2-fluorobenzyl)-4-hydroxypiperidin-4-yl]-methyl}-4-methyl-pyridin-2(1H)-one;

1-{[1-(4-fluorobenzyl)-4-hydroxypiperidin-4-yl]-methyl}-4-methyl-pyridin-2(1H)-one; and 1-{[1-(2,4-difluorobenzyl)-4-hydroxypiperidin-4-yl]-methyl}-4-methyl-pyridin-2(1H)-one;

or a tautomer thereof, a racemate or optical isomer thereof, a pharmaceutically acceptable salt or a solvate thereof.

The second aspect of the present invention relates to use of the compound of Formula I according to any item of the first aspect of the present invention, a tautomer, racemate or optical isomer, pharmaceutically acceptable salt or a solvate thereof, for the manufacturing of a medicament for the prevention or treatment of central nervous system diseases associated with 5-HT system dysfunction, such as depression, anxiety, mania, cognitive deficit, schizophrenia, Parkinson's disease, pain, drug dependence (or drug addiction) and relapse, various kinds of mental stress disorder and fear, anorexia, sleep disorder, sexual dysfunction, gastrointestinal dysfunction (e.g., nausea, vomiting, etc.), respiratory depression, kidney dysfunction, or endocrine and immune dysfunction, or a medicament as a tool drug for studying 5-HT function and diseases associated with 5-HT dysfunction.

The third aspect of the present invention provides use of the compound of Formula I according to any item of the first aspect of the present invention, a tautomer, racemate or optical isomer, pharmaceutically acceptable salt or a solvate thereof for the manufacturing of a medicament having 5-HT$_{1A}$R and 5-HT reuptake regulation activity.

The fourth aspect of the present invention provides a pharmaceutical composition, which comprises at least one of the compound of Formula I according to any item of the first aspect of the present invention, a tautomer thereof, a racemate or optical isomer thereof, a pharmaceutically acceptable salt thereof, and optionally a pharmaceutically acceptable carrier or excipient. According to this aspect, the present invention further relates to use of the pharmaceutical composition for the prevention or treatment of nervous system diseases associated with 5-HT system dysfunction (e.g., central nervous system diseases), such as depression, anxiety, mania, cognitive deficit, schizophrenia, Parkinson's disease, pain, drug dependence (or drug addiction) and relapse, various kinds of mental stress disorder and fear, anorexia, sleep disorder, sexual dysfunction, gastrointestinal dysfunction (e.g., nausea, vomiting, etc.), respiratory depression, kidney dysfunction, or endocrine and immune dysfunction, or as a tool drug for studying 5-HT function and diseases associated with 5-HT dysfunction.

The fifth aspect of the present invention provides a method for the prevention or treatment of nervous system diseases associated with 5-HT system dysfunction (e.g., central nervous system diseases), such as depression, anxiety, cognitive deficit, mania, schizophrenia, Parkinson's disease, pain, drug dependence (or drug addiction) and relapse, various kinds of mental stress disorder and fear, anorexia, sleep disorder, sexual dysfunction, gastrointestinal dysfunction (e.g., nausea, vomiting, etc.), respiratory depression, kidney dysfunction, or endocrine and immune dysfunction, or a method for studying 5-HT function and diseases associated with 5-HT dysfunction, the method comprises administrating a subject in need thereof a preventively and/or therapeutically effective amount of the compound of Formula I according to any item of the first aspect of the present invention, a tautomer thereof, a racemate or stereoisomer thereof, or a pharmaceutically acceptable salt thereof, or the method comprises using the compound of Formula I according to any item of the first aspect of the present invention, a tautomer thereof, a racemate or stereoisomer thereof, or a pharmaceutically acceptable salt thereof in an experiment for studying 5-HT function and diseases associated with 5-HT dysfunction.

The sixth aspect of the present invention provides a method for preparing the compound of Formula I according to any item of the first aspect of the present invention, a tautomer thereof, a racemate or optical isomer thereof, a pharmaceutically acceptable salt thereof, which comprises the following steps:

a) allowing a ketone compound of Formula II:

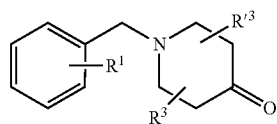

to be converted into an epoxide of Formula IIa by reacting with Me$_3$SI or Me$_3$SOI in the presence of a base:

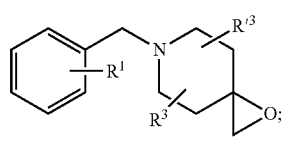

b) allowing the epoxide of Formula IIa as obtained in step a) to react with a hydroxy compound of Formula III under heating in the presence or absence of a catalyst:

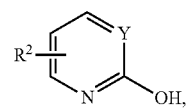

to obtain a compound of Formula I:

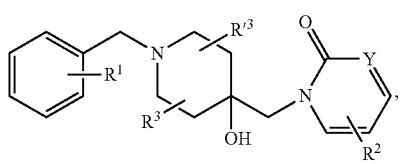

or allowing the epoxide of Formula IIa as obtained in step a) to react in the presence of water with an amine compound of Formula III' under heating in the presence or absence of a catalyst:

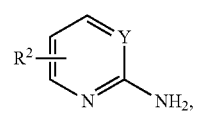

to obtain a compound of Formula I:

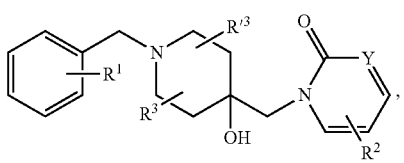

wherein the variables each are defined as for the compound of Formula I in any item of the first aspect of the present invention.

The method according to the sixth aspect of the present invention, wherein the carbonyl compound of Formula II is prepared in sequence by subjecting a corresponding benzylamine IV to addition with substituted methyl/ethyl acrylate V and V' to generate substituted benzylamines IV' and IV''', then subjecting IV''' to intramolecular ester condensation under the catalysis of a base, then saponification, and decarboxylation. Or, when the piperidine ring is not substituted, the carbonyl compound of Formula II' can also be prepared by reaction of a corresponding benzyl chloride VI or benzyl bromide VI' in the presence of a base.

Or, a) the compound of Formula I (R$^1$=H) reacts with phenyl chloroformate, then carries out basic hydrolysis to remove benzyl to obtain the following compound of Formula VII:

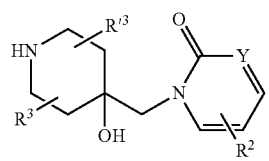

b) the compound of Formula VII reacts with a corresponding aldehyde for reductive alkylation, or reacts with a corresponding halogenide or sulfonate VI in the presence of a base to obtain the compound of Formula I:

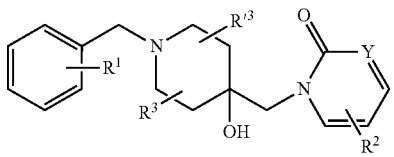

wherein the variables each are defined as for the compound of Formula I in any item of the first aspect of the present invention.

The seventh aspect of the present invention relates to a compound useful for the prevention or treatment of nervous system diseases associated with 5-HT system dysfunction (e.g., central nervous system diseases), such as depression, anxiety, mania, cognitive deficit, schizophrenia, pain, etc., or a compound useful as a tool drug for studying 5-HT function and diseases associated with 5-HT dysfunction, the compound is defined as the compound of Formula I according to any item of the first aspect of the present invention, a tautomer thereof, racemate or optical isomer, a pharmaceutically acceptable salt or a solvate thereof.

The eighth aspect of the present invention relates to a pharmaceutical composition useful for the prevention or treatment of nervous system diseases associated with 5-HT system dysfunction (e.g., central nervous system diseases), such as depression, anxiety, mania, cognitive deficit, schizophrenia, Parkinson's disease, pain, drug dependence (or drug addiction) and relapse, various kinds of mental stress disorder and fear, anorexia, sleep disorder, sexual dysfunction, gastrointestinal dysfunction (e.g., nausea, vomiting, etc.), respiratory depression, kidney dysfunction, endocrine and immune dysfunction, or useful as a tool drug for studying 5-HT function and diseases associated with 5-HT dysfunction, the pharmaceutical composition comprises as least one of the compound of Formula I according to any item of the first aspect of the present invention, a tautomer thereof, racemate or optical isomer, a pharmaceutically acceptable salt or a solvate thereof, and optionally a pharmaceutically acceptable carrier or excipient.

The features of any aspect of the present invention or any item of said any aspect are also suitable for any other aspect or any item of said any other aspect as long as they are not contradictory between each other, if necessary, the corresponding features being used between each other could be suitably modified. In the present invention, for example, when "any item of the first aspect of the present invention" is mentioned, the "any item" refers to any sub-aspect of the first aspect; and other aspects as mentioned in similar manner have the same meanings.

The aspects and features of the present invention are further described as follows.

DETAILED DESCRIPTION OF THE INVENTION

As for all documents as cited in the present invention, their contents are totally incorporated into the present invention by reference, and when the meanings of these documents are not consistent with those of the present invention, the expressions of the present invention are used. In addition, all terms and phrases used in the present invention have the general meanings well-known by those skilled in the art, nevertheless, it is still hoped to illustrate and explain these terms and phrases in details in the present invention, when the mentioned terms and phrases have meanings different from those well-known in the art, the meanings expressed in the present invention are use.

In the present invention, the term "halo", "halogen", "Hal" or "halogenated" refers to fluorine, chlorine, bromine, and iodine.

In the present invention, the terms "alkyl", "alkenyl" and "alkynyl" have the general meanings well-known in the art, which are straight or branched chain hydrocarbyl groups, such as, but not limited to methyl, ethyl, propyl, isopropyl, n-butyl, sec-butyl, tert-butyl, allyl, propenyl, propynyl, etc., and the "alkyl", "alkenyl" and "alkynyl" can be collectively called as "hydrocarbyl". In a preferable embodiment of the present invention, the "hydrocarbyl" refers to alkyl, including alkyl and cycloalkyl, especially alkyl, for example, $C_1$-$C_6$ alkyl.

As used in the present invention, the term "aryl" is, such as, but not limited to, phenyl, naphthyl.

As used in the present invention, the phrase "substituted or non-substituted $C_1$-$C_6$ alkyl" refers to a substituted or non-substituted alkyl group having specified number of carbon atoms, and its examples include but not limited to: methyl, ethyl, propyl, isopropyl, butyl, tert-butyl, pentyl, neopentyl, hexyl.

In the compound of Formula I of the present invention, when a substituent links to the internal part of ring, this represents that the substituent can substitute at any substitutable position of the ring, for example, when Y is CH in the oxo-aza ring, the ring is

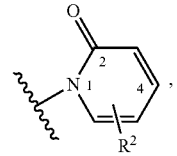

wherein the $R^2$ substituent can be at the 3-, 4-, 5-, or 6-position of the ring. In addition, for example, $R^2$ may be one or more substituents on the ring, for example, 2, 3, 4, 5 substituents on the ring, as long as the $R^2$ substituents on the ring meet the requirement of chemical valence. In the present invention, similar descriptions, for example, about $R^1$ substituent, have similar meanings.

In the present invention, the groups of "$C_1$-$C_6$ alkyl" and "$C_{1-6}$ alkyl" have the same meanings, and both represent straight or branched chain alkyl having 1-6 carbon atoms. Other similar situations can be similarly understood as well.

As for Y in the compound of Formula I, it each can be independently C or N. Those skilled in the art understand that Y should meet the requirement of chemical valence of the 6-membered ring in which it exists. For example, when $R^2$ is hydrogen, Y is C, the 6-membered ring forms pyridin-2(1H)-one ring, so that Y is —CH— radical; if Y is nitrogen, the 6-membered ring forms pyrimidin-2(1H)-one ring.

According to the first aspect of the present invention, in the compound of Formula I, $R^1$, $R^2$ are preferably H, fluorine, chlorine, bromine, methyl, ethyl, methoxy, ethoxy, dimethylamino, diethylamino, carbamoyl, or phenoxy; $R^3$, $R'^3$ are preferably H, methyl, ethyl, propyl, butyl, or 2-methoxy; Y is preferably CH or N.

According to the first aspect of the present invention, in the compound of Formula I, $R^1$ is preferably H, 2-fluoro, 4-fluoro, 2,3-difluoro, 2,4-difluoro, 2,5-difluoro or 2,6-difluoro; $R^2$ is preferably H, bromine or methyl; $R^3$ is preferably H, methyl, or 2-methoxy; Y is preferably CH or N.

The compounds of Formula I of the present invention are preferably the compounds of the following examples.

In the preferable embodiments of the present invention, the compounds are 1-[(1-benzyl-4-hydroxypiperidin-4-yl)-methyl]-pyridin-2(M)-one and 1-{[1-(2-fluorobenzyl)-4-hydroxypiperidin-4-yl]-methyl}-pyridin-2(1H)-one.

According to the teachings of the present invention, the compound of Formula I of the present invention can be synthesized according to the well-known knowledge in the art, i.e., prepared by Danzen reaction between a corresponding ketone and trimethylsulfonium bromide/iodide or sulfoxide to prepare a substituted epoxy IIa, and then reacting the epoxy IIa with a substituted 2-hydropyridine III in the presence or absence of a basic catalyst such as potassium carbonate or triethylamine; or prepared by reacting a corresponding epoxide IIa with a substituted 2-aminopyridine III' in the presence of water.

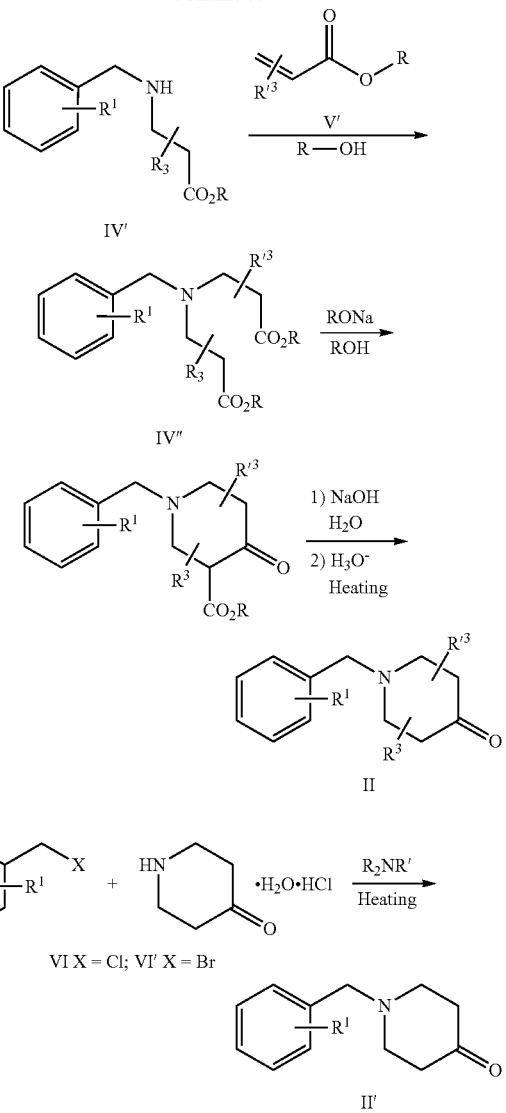

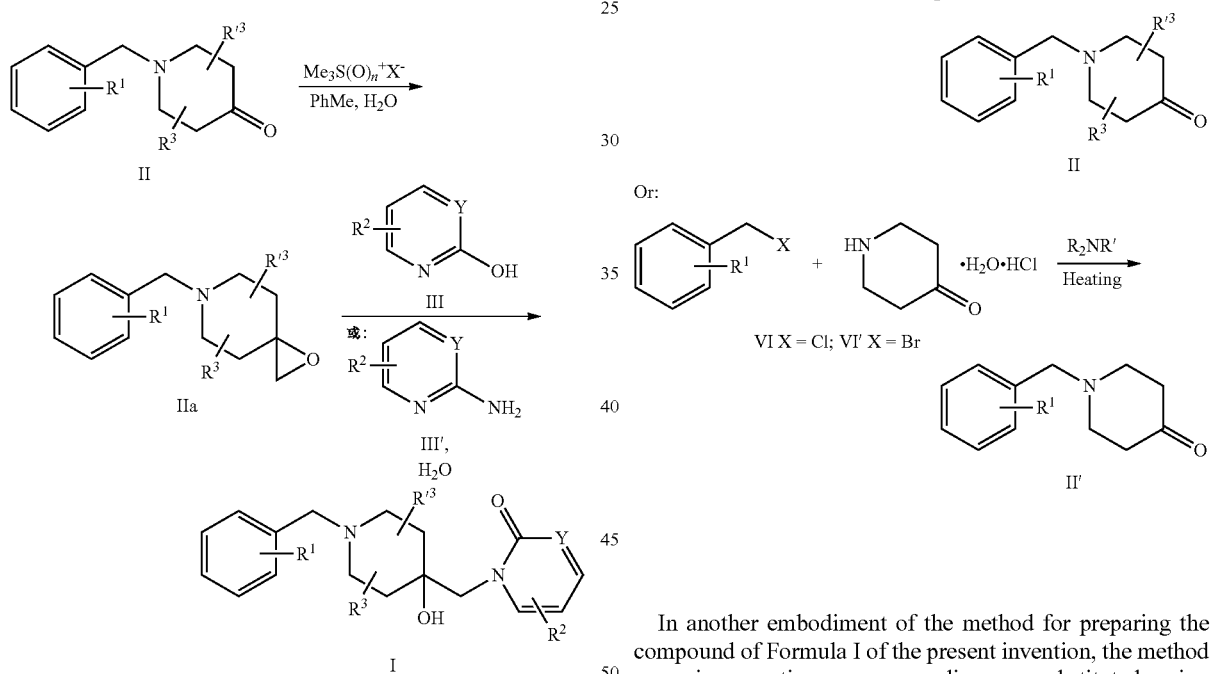

While the synthesis of ketone II can be performed in sequence by reacting a substituted benzylamine IV with corresponding acrylate V and V' to prepare N-substituted benzylamine IV' and IV'', and then further subjecting benzylamine IV''' to ester condensation, saponification and decarboxylic reaction to obtain corresponding ketone II; or by reacting a substituted benzyl chloride VI or benzyl bromide VI' with 4-piperidone hydrochloride in the presence of a base.

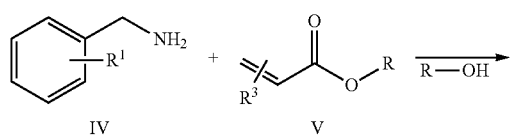

In another embodiment of the method for preparing the compound of Formula I of the present invention, the method comprises reacting a corresponding non-substituted amino alcohol $I_0(R_1=H)$ with phenyl chloroformate, then subjecting to basic hydrolysis to remove benzyl, to convert into 4,4-disubstituted piperidine VII, then subjecting the piperidine VII to reductive alkylation with a corresponding aldehyde or to alkylation with a corresponding halogenide or active ester to obtain the compound of Formula I.

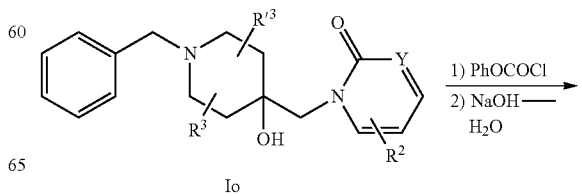

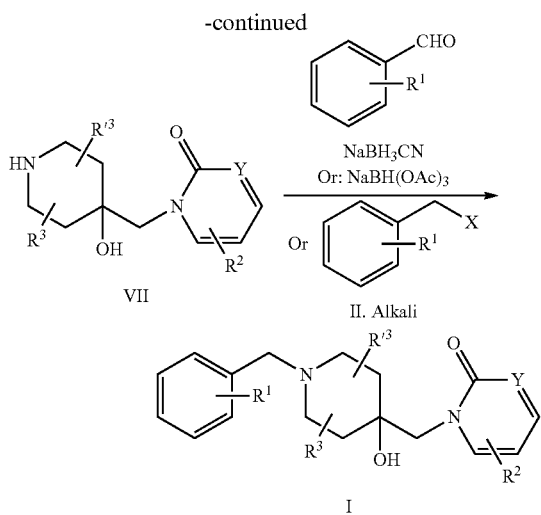

In the method of the present invention for the synthesis of the compound of Formula I, the various raw materials used in the reaction are obtainable by those skilled in the art according to the existing knowledge in the art, or can be prepared according to methods known in the documents, or are commercially available. The intermediates, raw materials, reagents and reaction conditions used in the reaction can be suitably modified according to the knowledge existing in the art. Or, those skilled in the art can also synthesize other compounds of Formula I tat are not listed in the present invention according to the second aspect of the present invention.

According to the present invention, the term "nervous system diseases associated with 5-hydroxytryptamine (5-HT) system dysfunction" refers to nervous system diseases (e.g., central nervous system diseases) caused directly or indirectly by 5-hydroxytryptamine (5-HT) system dysfunction, such as depression, anxiety, cognitive deficit, mania, schizophrenia, Parkinson's disease, pain, drug dependence (or drug addiction) and relapse, various kinds of mental stress disorder and fear, anorexia, sleep disorder, sexual dysfunction, gastrointestinal dysfunction (e.g., nausea, vomiting, etc.), respiratory depression, kidney dysfunction, or endocrine and immune dysfunction.

According to the present invention, the pharmaceutical acceptable salt of the compound of Formula I can be an acid addition salt or a salt formed with a base. The acid addition salt for example can be an inorganic acid salt, such as, but not limited to hydrochloride, sulfate, phosphate, hydrobromide; or an organic acid salt, such as, but not limited to acetate, oxalate, citrate, glyconate, succinate, tartrate, tosylate, mesylate, benzoate, lactate, maleate; the salt formed of the compound of Formula I with a base can be an alkali metal salt, such as, but not limited to salts of lithium, sodium and potassium; an alkaline earth metal salt, such as, but not limited to salts of calcium and magnesium; an organic base salt, such as, but not limited to a salt of diethanolamine and a salt of choline; or a chiral base salt, such as, but not limited to a salt of alkyl phenylamine The solvate of the compound of the present invention can be hydrate or include other crystal solvent such as alcohol, for example, ethanol.

According to the present invention, the compound of Formula I can include cis/trans isomers, and the present invention relates to these cis isomers and trans isomers as well as mixtures thereof. If necessary, a single stereoisomer can be prepared according to a conventional method for resolution of mixture, or via, for example, stereoselective synthesis. If there is a motive hydrogen atom, the present invention also relates to the tautomeric forms of the compound of Formula I.

According to the present invention, the compound of Formula I and stereoisomers thereof are useful in a medicament for the prevention or treatment of diseases associated with 5-HT system dysfunction, such as depression, anxiety, mania, cognitive deficit, schizophrenia, Parkinson's disease, pain, drug dependence (or drug addiction) and relapse, various kinds of mental stress disorder and fear, anorexia, sleep disorder, sexual dysfunction, gastrointestinal dysfunction (e.g., nausea, vomiting, etc.), respiratory depression, kidney dysfunction, or endocrine and immune dysfunction, wherein the medicament is used for an animal, preferably a mammal, especially human.

The present invention therefore further relates to a pharmaceutical composition comprising as an active component an effective amount of at least one of the compound of Formula I, or pharmaceutically acceptable salt thereof and/or stereoisomer thereof and conventional pharmaceutically excipient or adjuvant. The pharmaceutical composition of the present invention usually comprises 0.1-90 wt % of the compound of Formula I and/or physiologically acceptable salt. The pharmaceutical composition can be prepared according to the known method in the art. For this purpose, if necessary, the compound of Formula I and/or stereoisomer thereof is combined with one or more solid or liquid pharmaceutically acceptable excipients and/or adjuvants, to form an application form or dosage form suitable for administration to human.

The compound of Formula I of the present invention or the pharmaceutical composition containing the same can be administered in unit dosage form, and the administration routes can be intestinal or parenteral administration, such as oral, intramuscular, subcutaneous, nasal, oral mucosal, skin, intraperitoneal or rectal administration. The administration dosage form can be, for example, tablets, capsules, drop pills, aerosols, pills, powders, solutions, suspensions, emulsions, granules, liposomes, transdermal agents, buccal tablets, suppositories, lyophilized powder injections, can be normal preparations, sustained-release preparations, controlled-release preparations, and various microparticle administration systems. In order to process the unit dosage form into tablets, various carriers well known in the art can be widely used. The examples of the carriers can be, for example, diluents and absorbents, such as starch, dextrin, calcium sulfate, lactose, mannitol, sucrose, sodium chloride, glucose, urea, calcium carbonate, kaolin, microcrystalline cellulose, aluminum silicate; wetting agent and binding agent, such as water, glycerol, polyethylene glycol, ethanol, propanol, starch slurry, dextrin, syrup, honey, glucose solution, acacia mucilage, gelatin mucilage, sodium carboxymethylcellulose, shellac, methylcellulose, potassium phosphate, polyvinylpyrrolidone; disintegrants, such as, dry starch powder, alginate, agar powder, laminarin powder, sodium hydrogen carbonate and citric acid, calcium carbonate, polyoxyethylene sorbitol fatty acid ester, sodium dodecyl sulfate, methyl cellulose, ethyl cellulose; disintegration inhibitors, such as sucrose, tristearin, cocoa butter, hydrogenated oil; absorption enhancers, such as, quaternary ammonium salts, sodium dodecyl sulfate; lubricants, such as, talc, silica, maize powder, stearate, boric acid, liquid paraffin, polyethylene glycol. The tablets can be further processed into coated tablets, for example, sugar coated tablets, thin film coated tablets, enteric-coated tablets, or double-layer tablets or multi-layer tablets. In order to process the administration unit into pills, various carriers known in the art can be used. The examples of the carriers can be, for example, diluents and absorbing agents, such as glucose, lactose, starch, cocoa butter, hydrogenated vegetable oil, polyvinylpyrrolidone, Gelucire, kaolin, talc; binding agent, such as acacia gum, tragacanth gum, gelatin, ethanol, honey, liquid sugar, rice paste or panada; disintegrants, such as agar powder, dry starch powder, alginate, sodium dodecyl sulfonate, methyl cellulose, ethyl cellulose. In order to process the administration unit into suppositories, various carriers known in the art can be widely used. The examples of the carriers can be, for example, polyethylene glycol, lecithin, cocoa butter, fatty alcohol, ester of fatty alcohol, gelatin, semi-synthetic ester. In order to process the administration unit into capsules, the compound of Formula I or stereoisomer thereof as effective component is mixed with the various carriers, and the resultant mixture is placed in hard gelatin capsule shells or soft capsules. The compound of Formula I or stereoisomer thereof as effective component can also be processed into microcapsules, suspended in aqueous medium to form a suspension, or placed in hard capsules or processed into injections. In order to process the administration unit into a preparation for injection, such as solution, emulsion, lyophilized powder injection and suspension, all diluents known in the art, for example, water, ethanol, polyethylene glycol, 1,3-propylene glycol, ethoxylated isostearyl alcohol, multi-oxidized isostearyl alcohol, polyoxyethylene sorbitol fatty acid ester, could be used. In addition, in order to prepare an isotonic injection solution, an suitable amount of sodium chloride, glucose or glycerol can be added to the injection preparation, and conventional co-solvent, buffer agent, and pH regulator can further added.

In addition, if necessary, coloring agents, preservatives, flavoring agents, correctants, sweetening agents or other materials can also be added to the pharmaceutical preparations.

The administration dose of the compound of Formula I, or stereoisomer thereof may depend on many factors, for example, the properties and severity of the diseases to be prevented or treated, the gender, age, bodyweight and individual reaction of patient or animal, the specific compound to be used, the administration routes and times, and so on. The dose can be of single dose form or can be divided into several dose forms, such as, two, three or four dose forms.

The term "composition" used in the present invention refers to a product comprises designated ingredients in designated amounts, and any products directly or indirectly generated from the combination of designated ingredients in designated amounts.

The actual dose levels of active components in the pharmaceutical composition of the present invention can be modified to allow the resultant active compound amount achieve the desired therapeutic reaction according to specific patient, composition and administration route. The dose levels can be selected according to the activity of specific compound, administration route, the severity of disease to be treated, and the patient's condition and pasty medical history. However, the method in the art is that the dose of compound starts from a level lower than the requested level for achieving the desired therapeutic effects, then the dose gradually increases until the desired effects are achieved.

When using for the above treatment and/or prevention or other treatment and/or prevention, the compound of the present invention in a therapeutically and/or preventively effective amount can be used in pure form, or used in pharmaceutically acceptable ester or prodrug forms (in the situation these forms exist). Or, the compound can be administered in a pharmaceutical composition comprise the compound and one or more pharmaceutically acceptable excipients. The term "therapeutically and/or preventively effective amount" refers to an effective amount of compound suitable for any medical treatment and/or prevention with reasonable effectiveness/risk ratio in treatment of disorder. However, it should be understood, that the total daily dose of the compound and composition of the present invention can be determined by primary diagnostic doctor within reliable medical judgment extent. As for any specific patient, the specific therapeutically effective amount may depend on many factors, the factors include the disorder to be treated and the severity of the disorder; the activity of the specific compound to be used; the specific composition to be used; the age, bodyweight and general health conditions, gender and diet of patent; the administration time, administration routes and excretory rate of the specifically used compound; the duration of treatment; the drugs to used together or at the same time with the specific compound to be used; and similar factors known in the medical field. For example, the method in the art is that the dose of compound starts from a level lower than the requested level for achieving the desired therapeutic effects, then the dose gradually increases until the desired effects are achieved. In general, the dose of the compound of Formula I of the present invention to be used to mammal, especially human, is 0.001-1000 mg/kg bodyweight/day, for example, 0.01-100 mg/kg bodyweight/day, for example, 0.01-10 mg/kg bodyweight/day.

Beneficial Effects of the Invention

The compound according to the present invention can effectively prevent and/or treat the various diseases or disorder of the present invention.

MODE OF CARRYING OUT THE INVENTION

Figure 1:
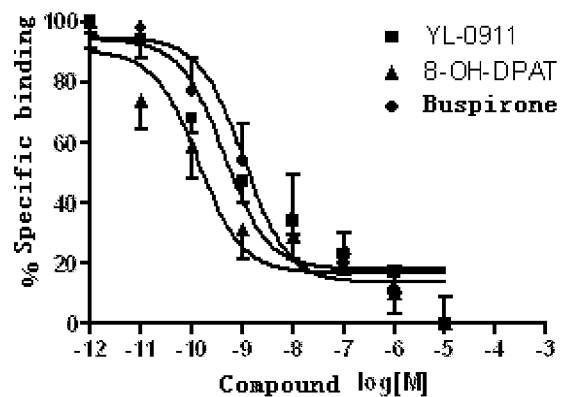
FIG. 1 represents the competitive binding curves of the Example compound 1 (YL-0911) of the present invention and the positive drugs buspirone, 8-OH-DPAT to 5-$HT_{1A}$ receptor radioligand.

The embodiments of the present invention are illustrated in details as follows in combination with examples, but those skilled in the art understand the following examples are merely used for explaining the invention, rather than limiting the scope of the present invention. When specific techniques or conditions are not explicated in examples, the techniques or conditions as described in the documents in the art or given in the product specifications are adopted. The used reagents or instruments which manufacturers are not given are all conventional products commercially available in markets.

Synthesis of Key Intermediates

1) N,N-bis(β-methoxycarbonylethyl)benzylamine

At room temperature, to a 500 mL three-necked bottle, 18.9 g (0.22 mol) of methyl acrylate and 100 mL of methanol were added, and a mixture solution of 10.7 g (0.1 mol) of benzylamine and 50 mL of methanol was slowly added dropwise to the three-necked bottle under stirring. The temperature was naturally elevated, and the addition rate was controlled so that the temperature of reaction system was not greater than 50° C. After the addition, the reaction was stirred at room temperature for 0.5 h, and reacted for 8 h under reflux. After completion of the reaction, the unreacted methanol and methyl acrylate were removed by vacuum distillation to obtain light yellow oily product N,N-bis(β-methoxy carbonylethyl)benzylamine, 27.3 g, yield 98%, by 174-176° C./533 Pa.

2) Synthesis of 1-benzyl-4-piperidone

To a 500 mL round bottom flask, 200 mL of anhydrous toluene and 4.5 g (0.11 mol) of sodium methoxide were added. The reaction was heated to 60° C. and stirred for a while, and 50 mL of toluene solution in which 28 g (0.1 mol) of N,N-bis(β-methyl propionate) benzylamine was dissolved was slowly added dropwise. The reaction solution quickly changed to be so viscous that the stirring speed increased. After the addition, the reaction was refluxed for 8 h. After completion of the reaction, the reflux was stopped, and the reaction was cooled to room temperature. A small amount of water was added to dissolve the undissolved substance. The reaction was stood for and separated to layers, and the toluene layer was extracted with concentrated hydrochloric acid (50 mL×3), and the water layer and the hydrochloric acid layers were combined. After and reacting under reflux for 6 h, the reaction was cooled to room temperature, and sodium hydroxide solution was added to regulate pH value to about 8-9. Extracted with ethyl acetate (100 mL×3), and the ethyl acetate layers were combined, washed once with saturated sodium chloride solution, and dried with anhydrous sodium sulfate, filtered, distilled under reduced pressure to recovery solvent to obtain light yellow oily liquid 1-benzyl-4-piperidone, 15 g, yield 80%, bp: 136-142° C./400 Pa. $^1$H-NMR (CDCl$_3$, ppm) δ: 7.32-7.34 (5H, m), 3.60 (2H, s), 2.72 (4H, s), 2.43 (4H, s).

3) Synthesis of trimethylsulfoxide iodide salt

To a 500 mL round bottom flask, 156 g (2 mol) of DMSO and 142 g (1 mol) of methyl iodide were added. The reaction was placed in a high performance refluxing device and reacted for 3 days. After completion of the reaction, the reaction was cooled, filtered, crystallized with water twice to obtain trimethylsulfoxide iodide salt, which is white crystal solid, 130 g, yield: about 60%, mp: 203° C. (sublimation).

4) Synthesis of N-benzyl-1-oxa-6-azaspiro[2,5]-octane 18.9 g (0.1 mol) of 1-benzyl-4-piperidone, 24.2 g (0.11 mol) of trimethylsulfoxide iodide salt, 0.5 g of tetrabutyl ammonium bromide and 200 mL of toluene were added to a 500 mL round bottom flask, and slowly added dropwise at room temperature with 60 mL of (15%) sodium hydroxide solution. Then the reaction was heated to 80° C., reacted for 8 h, and then cooled to room temperature. The toluene layer was separated, and the water layer was extracted with toluene (50 mL×3). The toluene layer was combined, washed with water, saturated sodium chloride solution in sequence, dried with anhydrous sodium sulfate, and distilled under reduced pressure to recovery solvent to obtain light yellow oily liquid N-benzyl-1-oxa-6-azaspiro[2,5]-octane 19 g, yield: 93%. $^1$H-NMR (CDCl$_3$, ppm) δ: 7.31-7.33 (5H, m), 3.56 (2H, s), 2.64 (2H, s), 2.53-2.62 (4H, m), 1.52-1.86 (4H, m).

5) Synthesis of 1-(2-fluorobenzyl)-4-piperidone 64.00 g (0.443 mol) of o-fluorobenzylchloride was weighed, to which 250 mL of dichloromethane was added. 62.40 g (0.406 mol) of 4-piperidone hydrochloride monohydrate was added under stirring, and then 91.00 g (0.899 mol) of triethylamine was added dropwise under cold water cooling and stirring. The reaction was stirred at room temperature for 4.5 h, and then stirred under reflux and reacted overnight. On the next day, the reaction was cooled, filtered to remove solid, washed in sequence with dichloromethane and ethyl ether, combined, washed with water and dried, and the solvent was recovered to obtain 68.95 g crude product (82.00%), which was used directly in the next reaction.

6) Synthesis of N-(2-fluorobenzyl)-1-oxa-6-azaspiro[2,5]-octane 68.95 g (0.333 mol) of 1-(2-fluorobenzyl)-4-piperidone crude product was added to a reaction bottle, and 290 mL of toluene was added. The reaction heated at 80° C. in an oil bath under stirring, and then to the reaction 83.00 g (0.377 mol) of trimethylsulfoxide iodide and 2.20 g (0.0065 mol) of tetrabutylammonium hydrogen sulfate was added in sequence. Then to the reaction 28.40 g (0.710 mol) sodium hydroxide dissolved in 90 mL of aqueous solution was added dropwise under stirring. After the addition, the reaction was stirred at 80° C. of bath temperature overnight. On the next day, the reaction was cooled, washed with water twice, extracted with a small amount of toluene, combined, and the solvent was recovered to obtain light yellow liquid, 54.70 g (74.2%), i.e., a crude target product. $^1$H-NMR (CDCl$_3$, ppm) δ: 7.394 (1H, dt, J$_1$=7.56 Hz, J$_2$=1.68 Hz), 7.254 (1H, m), 7.118 (1H, ddd, J$_1$=7.56 Hz, J$_2$=1.12 Hz), 7.037 (1H, dtd, J$_1$=8.96 Hz, J$_2$=1.12 Hz), 3.562 (2H, d, J=1.12 Hz), 2.647 (2H, s), 2.637 (4H, m), 1.820 (2H, m), 1.569 (2H, m).

7) Synthesis of 1-(4-fluorobenzyl)-4-piperidone 58.10 g (0.402 mol) of 4-fluorobenzylchloride was weighed, to which 250 mL of dichloromethane was added and then 62.00 g (0.404 mol) of 4-piperidone hydrochloride monohydrate was added. And then 86.00 g (0.850 mol) of triethylamine was added dropwise at 30-40° C. bath temperature under stirring. After the addition, the reaction was heated to reflux under stirring and reacted overnight. On the next day the reaction was cooled, filtered to remove solid, washed in sequence with dichloromethane and ethyl ether, combined, washed with water and dried, and the solvent was recovered to obtain 61.10 of crude product (73.3%), $^1$H-NMR (CDCl$_3$, ppm) δ: 7.322 (2H, m), 7.027 (2H, t, J=8.68 Hz), 3.585 (2H, s), 2.733 (4H, t, J=6.16 Hz), 2.441 (4H, t, J=6.16 Hz); which was used directed in the next step of reaction.

8) Synthesis of N-(4-fluorobenzyl)-1-oxa-6-azaspiro[2,5]-octane 61.00 g (0.295 mol) of 1-(4-fluorobenzyl)-4-piperidone crude product was added to a reaction bottle, to which 260 mL of toluene was added. The reaction was heated and stirred at 80° C. in an oil bath, and to the reaction 70.00 g (0.318 mol) of trimethylsulfoxide iodide and 2.70 g (0.0080 mol) of tetrabutylammonium hydrogen sulfate were added in sequence, then 28.00 g (0.700 mol) sodium hydroxide dissolved in 120 mL of aqueous solution was added dropwise under stirring. After the addition, the reaction was continuously stirred at 80° C. bath temperature overnight. On the next day, the reaction was cooled, washed with water twice, extracted with a small amount of toluene, combined and dried, and the solvent was recovered to obtain light yellow liquid, 47.50 g (72.8%), i.e., a crude target product, $^1$H-NMR (CDCl$_3$, ppm) δ: 7.298 (2H, m), 7.007 (2H, m), 3.519 (2H, s), 2.565 (2H, s), 2.559 (4H, m), 1.827 (2H, m), 1.534 (2H, m).

9) Synthesis of 1-(2,4-difluorobenzyl)-4-piperidone 28.20 g (0.125 mol) of 2,4-difluorobenzyl bromide was weighed, to which 200 mL of dichloromethane was added and then 62.00 g (0.404 mol) of 4-piperidone hydrochloride monohydrate was added under stirring. And then 86.00 g (0.850 mol) of triethylamine was added dropwise at a bath temperature of 30-40° C. under stirring. After the addition, the reaction was heated, refluxed and reacted overnight. On the next day, the reaction was cooled, filtered to removed solid, washed in sequence with dichloromethane and ethyl ether, combined, washed with water and dried, and the solvent was recovered to obtain 61.10 g of crude product (73.3%), $^1$H-NMR (CDCl$_3$, ppm) δ: 7.31-7.33 (5H, m), 3.56 (2H, s), 2.64 (2H, s), 2.53-2.62 (4H, m), 1.52-1.86 (4H, m); which was used directly in the next step of reaction.

10) Synthesis of N-(2,4-difluorobenzyl)-1-oxa-6-azaspiro[2,5]-octane 28.20 g (0.125 mol) of 1-(2,4-difluorobenzyl)-4-piperidone crude product was added to a reaction bottle, to which 200 mL of toluene was added. The reaction was heated and stirred at 80° C. in an oil bath, and to the reaction 29.60 g (0.135 mol) of trimethylsulfoxide iodide and 0.60 g (0.0018 mol) of tetrabutylammonium hydrogen sulfate were added in sequence and then 11.40 g (0.285 mol) of sodium hydroxide dissolved in 60 mL of aqueous solution was added dropwise under stirring. After the addition, the reaction was continuously stirred at bath temperature of 80° C. overnight. On the next day, the reaction was cooled, washed with water twice, extracted with a small amount of toluene, combined and dried, and the solvent was recovered to obtain light yellow liquid 22.00 g (73.6%), i.e., a crude target product, $^1$H-NMR (CDCl$_3$, ppm) δ: 7.361 (1H, m), 6.76-6.89 (2H, m), 3.597 (2H, d, J=1.12 Hz), 2.651 (2H, s), 2.601 (4H, m), 1.829 (2H, m), 1.545 (2H, m).

EXAMPLE 1

Preparation of 1-[(1-benzyl-4-hydroxypiperidin-4-yl)-methyl]-pyridin-2(1H)-one (Compound 1, also Called as YL-0911 in the Present Invention)

Method 1: 102.00 g of (0.501 mol) N-benzyl-1-oxa-6-azaspiro[2,5]-octane and 48.20 g (0.512 mol) of 2-aminopyridine were weighed, to which 256 mL of ethylene glycol monomethyl ether and 25 mL of water were added. The reaction was stirred at a bath temperature of about 80° C. and reacted for 2 days. TLC showed that there was still a lot of unreacted raw materials, and then the reaction was heated to 100° C. and reacted for further 1 day, cooled to room temperature, distilled under reduced pressure to remove solvent. 260 mL of ethanol and 37.20 g of fumaric acid were further added to the reaction and then the reaction was heated and stirred for dissolution thereof, naturally cooled to 45° C. 30 mL of anhydrous ethyl ether was added and the reaction was stood for and a solid was precipitated. The solid was filtered and washed with a small amount of isopropanol. The filtrate and washing solution were combined and distilled under reduced pressure to recovery solvent. 100 mL of water was added and the mixture was basified with 20.20 g of sodium hydroxide and 14.20 g of anhydrous sodium acetate, extracted with dichloromethane (80 mL×3), washed with water and dried, and the solvent was recovered. The residue was separated by silica gel column chromatograph, eluted with 0-10% methanol-dichloromethane in gradient manner. The relatively polar main component was collected, distilled under reduced pressure to remove solvent, and crystallized using petroleum ether-tetrahydrofuran to obtain light yellow sand like crystal, which was dried to give about 48.50 g of solid, yield 32.6%. Melting point: 137-139° C. $^1$H-NMR (CDCl$_3$, ppm) δ: 7.396 (1H, hept, J=6.72, 2.24 Hz), 7.22-7.34 (6H, m), 6.641 (1H, dd→d, J=8.92 Hz), 6.231 (1H, txd, J=6.72, 1.4 Hz), 4.753 (1H, s), 4.045 (2H, s), 3.530 (2H, s), 2.663 (2H, br-t), 2.401 (2H, td), 1.56-1.76 (4H, m). Hydrochloride: 39.00 g of crystal was dissolved in THF-EtOH (3:1), and salified using HCl-EtOH to obtain a colorless granule crystal, 38.35 g, yield 79.0%. Melting point: 216-218° C. HR-MS (m/z, TOF): C$_{18}$H$_{23}$N$_2$O$_2$, theoretical value: 299.17595, measured value: 299.17649.

Method 2: 43.50 g (0.214 mol) of N-benzyl-1-oxa-6-azaspiro[2,5]-octane and 19.90 g (0.209 mol) of 2-hydroxy-pyridine were weighed and added into 85 mL of N,N-dimethylformamide, and then 3.25 g (0.024 mol) of potassium carbonate was added. The reaction was stirred and reacted at bath temperature of about 80° C. for 1 day, and the solvent was recovered under reduced pressure. Potassium carbonate aqueous solution was added into the residue. The mixture was extracted with dichloromethane twice, combined, washed with water and dried. The solvent was recovered and the residue was crystallized with petroleum ether-ethyl acetate to obtain a colorless flake-like crystal, 46.80 g, yield 56.2%. Melting point: 137-139° C. $^1$H-NMR (CDCl$_3$, ppm) δ: 7.392 (1H, hept, J=6.72, 2.24 Hz), 7.22-7.34 (6H, m), 6.638 (1H, dd→d, J=8.92 Hz), 6.232 (1H, txd, J=6.72, 1.4 Hz), 4.751 (1H, s), 4.041 (2H, s), 3.526 (2H, s), 2.660 (2H, br-t), 2.398 (2H, td), 1.56-1.76 (4H, m). Hydrochloride: 43.00 g of the crystal was dissolved with EtOAc-EtOH (3:1) and then salified with HCl-EtOH to obtain a colorless fine granular crystal 40.50 g, yield 86.3%. Melting point: 217-219° C.

EXAMPLE 2

Preparation of 1-{[1-(2-fluorobenzyl)-4-hydroxypiperidin-4-yl]-methyl}-pyridin-2(1H)-one (Compound 2)

23.00 g (0.104 mol) of N-(2-fluorobenzyl)-1-oxa-6-azaspiro[2,5]-octane and 10.30 g (0.108 mol) of 2-hydroxy-pyridine were weighed and added into 80 mL N,N-dimethylformamide, and then 1.00 g (0.007 mol) potassium carbonate was added. The reaction was stirred and reacted at a bath temperature of about 80° C. for 1 day, and the solvent was recovered. Potassium carbonate aqueous solution was added into the residue The mixture was extracted with dichloromethane twice, combined, washed with water, and dried. The solvent was recovered, crystallized with petroleum ether-ethyl acetate to obtain colorless flake-like crystal, 22.80 g, yield 69.3%. $^1$H-NMR (CDCl$_3$, ppm) δ: 7.372 (2H, m), 7.228 (2H, m), 7.092 (1H, t, J=7.56 Hz), 7.020 (1H, t, J=8.96 9.24 Hz), 6.639 (1H, d, J=9.24 Hz), 6.228 (1H, txd, J$_1$=6.72 Hz, J$_2$=1.12 Hz), 4.720 (1H, s), 4.036 (2H, s), 3.603 (2H, s), 2.69 (2H, dd, J$_1$=7.84 Hz, J$_2$=3.64 Hz), 2.46 (2H, txd, J$_1$=8.40 Hz, J$_2$=2.80 Hz), 1.55-1.74 (4H, m). The product was heated and dissolved in ethanol-ethyl acetate, salified with HCl-EtOH while warm and naturally cooled to obtain a colorless fine granular crystal, which was dried under vacuum to obtain 20.00 g product. Melting point: 249-251° C.

EXAMPLE 3

Preparation of 1-{[1-(4-fluorobenzyl)-4-hydroxypiperidin-4-yl]-methyl}-pyridin-2(1H)-one (Compound 3)

4.47 g (0.0202 mol) of N-(4-benzyl)-1-oxa-6-azaspiro[2,5]-octane and 2.03 g (0.0213 mol) of 2-hydroxypyridine were weighed and added into 60 mL of N,N-dimethylformamide, and then 0.18 g (0.0013 mol) of potassium carbonate was added. The reaction was stirred and reacted at a bath temperature of about 80° C. for 1 day and the solvent was recovered under reduced pressure. Potassium carbonate aqueous solution was added to the residue and the mixture was extracted with dichloromethane twice, combined, washed with water and dried, and the solvent was recovered. The residue was crystallized with petroleum ether-ethyl acetate to obtain a colorless flake-like crystal, 4.92 g, yield 77.0%. Melting point: 154-156° C. $^1$H-NMR (CDCl$_3$, ppm) δ: 7.392 (1H, tdt, J$_1$=7.84 Hz, J$_2$=2.24 Hz), 7.22-7.29 (3H, m), 6.988 (2H, t×t, J$_1$=8.68 Hz, J$_2$=1.96 Hz), 6.642 (1H, dd→d, J=8.40 Hz), 6.232 (1H, t×d, J$_1$=6.72 Hz, J$_2$=1.40 Hz), 4.729 (1H, s), 4.042 (2H, s), 3.484 (2H, s), 2.699 (2H, dd, J$_1$=7.56 Hz, J$_2$=3.92 Hz), 2.381 (2H, t×d, J$_1$=10.93 Hz, J$_2$=3.08 Hz), 1.55-1.70 (4H, m). 3.84 g of free base was weighed, heated and dissolved in ethanol-ethyl acetate, salified with HCl-EtOH while warm and naturally cooled to obtain a colorless fine granular crystal, which was dried under vacuum to obtain 5.35 g product. Melting point: 166-168° C., yield: 97.6%.

EXAMPLE 4

1-{[1-(2,4-difluorobenzyl)-4-hydroxypiperidin-4-yl]-methyl}-pyridin-2(1H)-p-one (Compound 4)

2.40 g (0.0200 mol) of N-(2,4-benzyl)-1-oxa-6-azaspiro[2,5]-octane and 2.00 g (0.0210 mol) of 2-hydroxypyridine were weighed and added into 40 mL of N,N-dimethylformamide, and then 0.25 g (0.0018 mol) of potassium carbonate was added. The reaction was stirred and reacted at a bath temperature of about 80° C. for 1 day and the solvent was recovered under reduced pressure. Potassium carbonate aqueous solution was added to the residue and the mixture was extracted with dichloromethane twice, combined, washed with water and dried, and the solvent was recovered. The residue was crystallized with petroleum ether-ethyl acetate to obtain a colorless flake-like crystal, 3.64 g, yield 54.4%. Melting point: 136-138° C. $^1$H-NMR (CDCl$_3$, ppm) δ: 7.33-7.43 (2H, m), 7.228 (1H, dd, J$_1$=6.72 Hz, J$_2$=1.68 Hz), 6.75-6.88 (2H, m), 6.643 (1H, dd, J$_1$=8.40 Hz, J$_2$=0.56 Hz), 6.235 (1H, t×d, J$_1$=6.72 Hz, J$_2$=1.40 Hz), 4.808 (1H, s), 4.041 (2H, s), 3.587 (2H, s), 2.690 (2H, dd→d, J=11.20 Hz), 2.381 (2H, t×d→t, J$_1$=9.52 Hz, J$_2$=11.48 Hz), 1.56-1.72 (4H, m). 3.40 g of the crystal was taken, heated and dissolved in ethanol-ethyl acetate, salified with HCl-EtOH while warm and naturally cooled to obtain a colorless fine granular crystal, which was dried under vacuum to obtain 2.80 g product. Melting point: 178-180° C., yield: 75.5%.

EXAMPLE 5

Preparation of 5-bromo-1-[(1-benzyl-4-hydroxypiperidin-4-yl)-methyl]-pyridin-2(1H)-one (Compound 5)

Referring to the method 2 of Example 1, N-benzyl-1-oxa-6-azaspiro[2,5]-octane and 5-bromo-2-hydroxy-pyridine were used for preparing a free base. Melting point: 146-148° C. The product was dissolved in ethanol-ethyl acetate and salified with HCl-EtOH to obtain a hydrochloride, yield 78.5%. Melting point: 148-150° C. $^1$H-NMR (D$_2$O, ppm) δ: 7.594 (1H, d, J=2.80 Hz), 7.495 (1H, dd, J$_1$=9.52 Hz, J$_2$=2.52 Hz), 7.24-7.34 (5H, m), 6.365 (1H, d, J=9.52 Hz), 4.112 (2H, s), 3.891 (2H, s), 3.208 (2H, d, J=13.15 Hz), 3.031 (2H, t, J$_1$=11.20 Hz, J$_2$=12.60 Hz), 1.742 (2H, t×d, J$_1$=11.20 Hz, J$_2$=3.95 Hz), 1.573 (2H, J=14.57 Hz).

EXAMPLE 6

Preparation of 5-bromo-1-{[1-(2-fluorobenzyl)-4-hydroxypiperidin-4-yl]-methyl}-pyridin-2(1H)-one (Compound 6)

7.00 g (0.0316 mol) of N-(2-fluorobenzyl)-1-oxa-6-azaspiro[2,5]-octane and 5.50 g (0.0314 mol) of 5-bromo-2-hydroxy-pyridine were weighed and added into 40 mL of N,N-dimethylformamide, and then 0.53 g (0.004 mol) of potassium carbonate was added. The reaction was stirred and reacted at a bath temperature of about 80° C. for 1 day and the solvent was recovered under reduced pressure. Potassium carbonate aqueous solution was added to the residue and the mixture was extracted with dichloromethane twice, combined, washed with water and dried, and the solvent was recovered. The residue was crystallized with petroleum ether-ethyl acetate to obtain a colorless flake-like crystal, 4.20 g, yield 69.3%. $^1$H-NMR (CDCl$_3$, ppm) δ: 7.413 (1H, s), 7.399 (1H, dd, J$_1$=8.20 Hz, J$_2$=2.80 Hz), 7.358 (1H, t×d, J$_1$=7.28 Hz, J$_2$=1.68 Hz), 7.229 (1H, m), 7.096 (1H, t×d, J$_1$=7.56 Hz, J$_2$=1.12 Hz), 7.021 (1H, hept→t, J$_1$=9.80 Hz), 6.543 (1H, dd, J=8.12 Hz), 3.994 (2H, s), 3.848 (1H, s), 3.602 (2H, s), 2.699 (2H, dd, J$_1$=7.56 Hz, J$_2$=3.82 Hz), 2.46 (2H, t×d, J$_1$=8.96 Hz, J$_2$=2.52 Hz), 1.54-1.74 (4H, m). The product was heated and dissolved in ethanol-ethyl acetate, salified with HCl-EtOH while warm and naturally cooled to obtain a colorless fine granular crystal, which was dried under vacuum to obtain 4.60 g product. Melting point: 184-186° C.

EXAMPLE 7

Preparation of 5-bromo-1-{[1-(4-fluorobenzyl)-4-hydroxypiperidin-4-yl]-methyl}-pyridin-2(M)-one (Compound 7)

4.43 g (0.0200 mol) of N-(4-fluorobenzyl)-1-oxa-6-azaspiro[2,5]-octane and 3.55 g (0.0202 mol) of 5-bromo-2-hydroxy-pyridine were weighed and added into 40 mL of N,N-dimethylformamide, and then 0.15 g (0.0011 mol) of potassium carbonate was added. The reaction was stirred and reacted at a bath temperature of about 80° C. for 1 day and the solvent was recovered under reduced pressure. Potassium carbonate aqueous solution was added to the residue and the mixture was extracted with dichloromethane twice, combined, washed with water and dried, and the solvent was recovered. The residue was crystallized with petroleum ether-ethyl acetate to obtain a colorless flake-like crystal, 2.65 g, yield 33.2%. Melting point: 181-183° C. $^1$H-NMR (CDCl$_3$, ppm) δ: 7.419 (1H, s), 7.405 (1H, dd, J$_1$=9.80 Hz, J$_2$=2.52 Hz), 7.252 (1H, t, J=8.68 Hz), 6.990 (2H, t, J=8.68 Hz), 6.547 (1H, d, J=9.80 Hz), 4.000 (2H, s), 3.864 (1H, s), 3.480 (2H, s), 2.641 (2H, dd, J$_1$=7.84 Hz, J$_2$=3.92 Hz), 2.352 (2H, t×d, J$_1$=9.84 Hz, J$_2$=1.96 Hz), 1.53-1.73 (4H, m). 2.65 g of free base was weighed, heated and dissolved in ethanol-ethyl acetate, salified with HCl-EtOH while warm and naturally cooled to obtain a colorless fine granular crystal, which was dried under vacuum to obtain 2.29 g product. Melting point: 255-257° C., yield: 80%.

EXAMPLE 8

Preparation of 5-bromo-1-{[1-(2,4-fluorobenzyl)-4-hydroxypiperidin-4-yl]-methyl}-pyridin-2(M)-one (Compound 8)

Referring to the method 2 of Example 1, N-(2,4-fluorobenzyl)-1-oxa-6-azaspiro[2,5]-octane and 5-bromo-2-hydroxy-pyridine were used as raw materials for preparing a free base. Melting point: 172-174° C. The product was dissolved in ethanol-ethyl acetate, salified with HCl-EtOH to obtain a hydrochloride. Melting point: 271-273° C., $^1$H-NMR (D$_2$O, ppm) δ: 7.601 (1H, s), 7.508 (1H, d, J=9.52 Hz), 7.330 (1H, q, J$_1$=8.12 Hz, J$_2$=6.44 Hz), 6.884 (1H, q, J$_1$=8.40 Hz, J$_2$=7.00 Hz), 6.365 (1H, d, J=9.52 Hz), 4.175 (2H, s), 3.904 (2H, s), 3.262 (2H, d, J=11.76 Hz), 3.081 (2H, t, $J_1$=12.32 Hz, $J_2$=12.60 Hz), 1.742 (2H, t×d→t, $J_1$=11.20 Hz, $J_2$=13.44 Hz), 1.593 (2H, J=14.56 Hz).

EXAMPLE 9

Preparation of 1-[(1-benzyl-4-hydroxypiperidin-4-yl)-methyl]-4-methylpyridin-2(M)-one (Compound 9)

2.23 g (0.0202 mol) of N-(4-benzyl)-1-oxa-6-azaspiro[2,5]-octane and 1.13 g (0.0208 mol) of 2-hydroxy-4-methylpyridine were weighed and added into 50 mL of anhydrous methanol, then 0.18 g (0.0013 mol) of potassium carbonate was added. The reaction was stirred and reacted at a bath temperature of about 70° C. for 1 day and the solvent was recovered under reduced pressure. Potassium carbonate aqueous solution was added to the residue and the mixture was extracted with dichloromethane twice, combined, washed with water and dried, and the solvent was recovered. The residue was crystallized with petroleum ether-ethyl acetate to obtain a colorless flake-like crystal, 0.63 g, yield 20.2%. Melting point: 145-146° C. $^1$H-NMR (CDCl$_3$, ppm) δ: 7.25-7.35 (5H, m), 7.105 (1H, d, J=7.00 Hz), 6.438 (1H, s), 6.076 (1H, d, J=6.72 Hz), 5.004 (1H, s), 4.005 (2H, s), 3.550 (2H, s), 2.673 (2H, dd→d, J=11.48 Hz), 2.381 (2H, t×d→t, $J_1$=9.24 Hz, $J_2$=11.20 Hz), 2.203 (3H, s), 1.54-1.70 (4H, m). The product was heated and dissolved in ethanol-ethyl acetate, salified with HCl-EtOH while warm and naturally cooled to obtain a colorless fine granular crystal, which was dried under vacuum to obtain 0.68 g product. Melting point: 220-222° C.

EXAMPLE 10

Preparation of 1-{[1-(2-fluorobenzyl)-4-hydroxypiperidin-4-yl]-methyl}-4-methylpyridin-2(M)-one (Compound 10)

Referring to the method of Example 9, N-(2-fluorobenzyl)-1-oxa-6-azaspiro[2,5]-octane and 2-hydroxy-4-methylpyridine were used as raw materials for synthesis to obtain 2.69 g product, yield 40.8%. Melting point: 122-124° C. $^1$H-NMR (CDCl$_3$, ppm) δ: 7.390 (1H, t, J=6.86 Hz), 7.21-7.27 (1H, m), 7.07-7.13 (2H), 7.023 (1H, t, $J_1$=9.80 Hz, $J_2$=8.68 Hz), 6.433 (1H, s), 6.072 (1H, dd, $J_1$=7.01 Hz, $J_2$=1.68 Hz), 5.017 (1H, s), 3.997 (2H, s), 3.633 (2H, s), 2.705 (2H, dd→d, J=11.48 Hz), 2.507 (2H, t×d→t, $J_1$=9.52 Hz, $J_2$=10.92 Hz), 2.201 (3H, s), 1.55-1.72 (4H, m). The product was heated and dissolved in ethanol-ethyl acetate, salified with HCl-EtOH while warm and naturally cooled to obtain a colorless fine granular crystal, which was dried under vacuum to obtain 2.85 g product. Melting point: 190-192° C.

EXAMPLE 11

Preparation of 1-{[1-(4-fluorobenzyl)-4-hydroxypiperidin-4-yl]-methyl}-4-methylpyridin-2(M)-one (Compound 11)

Referring to the method of Example 9, N-(4-fluorobenzyl)-1-oxa-6-azaspiro[2,5]-octane and 2-hydroxy-4-methylpyridine were used as raw materials for synthesis to obtain 0.90 g product, yield 27.3%. Melting point: 154-156° C. $^1$H-NMR (CDCl$_3$, ppm) δ: 7.309 (2H, m), 7.104 (1H, d, J=6.72 Hz), 7.000 (2H, m), 6.438 (1H, d→s), 6.081 (1H, dd, $J_1$=7.00 Hz, $J_2$=1.96 Hz), 5.094 (1H, br-s), 4.006 (2H, s), 3.530 (2H, d, J=6.72 Hz), 2.677 (2H, dd→d, J=11.20 Hz), 2.453 (2H, t×d→t, $J_1$=10.36 Hz, $J_2$=12.05 Hz), 2.204 (3H, d, J=10.84 Hz), 1.55-1.72 (4H, m). The product was heated and dissolved in ethanol-ethyl acetate, salified with HCl-EtOH while warm and naturally cooled to obtain a colorless fine granular crystal, which was dried under vacuum to obtain 0.94 g product. Melting point: 250-251° C.

EXAMPLE 12

Preparation of 1-{[1-(2,4-difluorobenzyl)-4-hydroxypiperidin-4-yl]-methyl}-4-methylpyridin-2(M)-one (Compound 12)

Referring to the method of Example 9, N-(2,4-difluorobenzyl)-1-oxa-6-azaspiro[2,5]-octane and 2-hydroxy-4-methylpyridine were used as raw materials for synthesis to obtain 0.58 g product, yield 16.7%. Melting point: 157-158° C. $^1$H-NMR (CDCl$_3$, ppm) δ: 7.356 (1H, dd→q, $J_1$=8.40 Hz, $J_2$=6.72 Hz), 7.094 (1H, d, J=7.00 Hz), 6.75-6.87 (2H, m), 6.437 (1H, s), 6.079 (1H, d, $J_1$=7.00 Hz, $J_2$=1.96 Hz), 5.040 (1H, br-s), 3.996 (2H, s), 3.580 (2H, s), 2.678 (2H, dd→d, J=11.48 Hz), 2.381 (2H, t×d, $J_1$=11.20 Hz, $J_2$=2.52 Hz), 2.204 (3H, d, J=10.84 Hz), 1.54-1.70 (4H, m). The product was heated and dissolved in ethanol-ethyl acetate, salified with HCl-EtOH while warm and naturally cooled to obtain a colorless fine granular crystal, which was dried under vacuum to obtain 0.59 g. Melting point: 207-210° C.

The following biological activity experiments are used for further illustrating the present invention.

Biological Effect Experiment 1: Radioligand competition binding test of 5-HT$_{1A}$ receptor and 5-HT transport protein 1.1 Mechanism A radioactive isotope-labeled ligand and a receptor-containing membrane protein were incubated under suitable conditions, so that the receptor and the ligand were sufficiently bond to form a complex.

When [R] was fixed and unchanged and [L*] is sufficiently large, [RL] binding reached saturated, then removed unbound free radioligand, and intensity of radiation was measured.

Specific binding CPM number=total binding CPM number−nonspecific binding CPM number (each binding took duplicated tubes)

$$\text{Inhibition percent (\%)} = \frac{\text{total binding } CPM \text{ number} - \text{dosing tube } CPM \text{ number}}{\text{total binding } CPM \text{ number} - \text{specific binding } CPM \text{ number}} \times 100\%$$

1.2 Experimental Materials:

(1) Membrane proteins each extracted from different cell lines which stably express 5-HT$_{1A}$ receptor, 5-HT transport protein (SERT), NE transport protein (NET).

(2) Crudely produced synaptosomes extracted from hippocampi and anterior cortex of rats.

(3) High speed refrigerated centrifuge, HIACHI (Model: 20PR-5).

(3) Super speed refrigerated centrifuge, HIACHI (Model: SCP85H).

(4) Homogenizer, ULTRA-TURRAXT25.

(5) UV-250 ultraviolet spectrophotomer, Shimadzu Co., Japan.

(6) Twenty-well cell harvester, Shaoxing Instrument Device Co.

(7) 49-Type glass fiber filtration membrane, Shanghai Yuguang Clarification Material Corporation.

(8) LS6500 Type Liquid Scintillation Counter, Beckman Company.

(9) Culture dish, 12-well plate, 96-well plate, Corning Company.

1.3 Reagents:

(1) [$^3$H]-8-OH-DPAT, [$^3$H]-citalopram, [$^3$H]-nisoxetine, [$^3$H]-5-HT, which are products of PE Company.

(2) WAY100635, fluoxetine, reboxetine, duloxetine, desipamine, buspirone, which are products of Sigma Company.

(3) Methyllycaconitine (MLA), Polyethyleneimine (PEI), bovine serum albumin (BSA), PMSF, proteinase inhibitors, which are products of Sigma Company.

(4) Scintillation fluid, which is product of PE Company.

(5) Folin-phenol reagent, which is a product of Huawei Keyi Company.

(6) Tris-HCl buffer solution (50 mM Tris-HCl, 1 mM EDTA, 5 mM MgCl$_2$, 1 mM PMSF, 0.1% NaN$_3$, 3 µg/ml proteinase inhibitor, pH 7.4).

(7) HEK-293 cell line, which is purchased from School of Basic Medicine Peking Union Medical College.

(8) 5-HT transport protein (SERT) and NE transport protein (NET), which are two plasmids purchased from Addgene Company, USA.

(9) Other reagents are all analytical pure reagents.

1.4 Experimental Methods 1.4.1 Screening of YL Series Compounds (1) Preparation of Membrane Proteins in Rat Hippocampi Wister rats, 220-260 g, female and male, were sacrificed by decapitation and hippocampis were rapidly separated, weighed and to which homogenized in 10 times volume of Tris-HCl buffer solution (50 mM Tris-HCl, 5 mM MgCl$_2$,1 mM EDTA, 0.5% (WN) BSA, 1 mM PMSF, 3 µg/ml proteinase inhibitor, 0.1% NaN$_3$, 0.32M sucrose, pH 7.4) at 15,000 rpm for 30 s, total 5 times. The homogenate was centrifuged under 1000×g for 10 minutes and the supernatant was then centrifuged under 39000×g for 10 minutes. The precipitate was collected, and resuspended with 10 times volume of Tris-HCl buffer solution (pH 7.4) relative to the original weight, then centrifuged under 39000×g for 10 minutes. The precipitate was washed with the same buffer solution, centrifuged under 39000×g for 10 minutes and the precipitate was suspended with the above buffer solution. After sub-packaged (the whole operation procedures were performed under ice bath), the product was stored at −80° C. The protein concentration was measured by Lowrry method.

(2) Competitive Binding Test of the Compound to be Tested as Binding to SERT (Using [$^3$H]-citalopram) and 5-HT$_{1A}$ Receptor (Using [$^3$H]-8-OH-DPAT)

1) In the 5-HT$_{1A}$ receptor binding test, tubes are firstly placed under reaction condition of 25° C.

2) To all of the tubes, the receptor proteins extracted from rat hippocampi in an amount of 100 µg were added in sequence.

3) To the nonspecific binding tubes, 50 µl (final concentration: 25 µM) of Way100635 was added, which was pre-reacted for 30 min.

4) To the test tubes, 30 µl of the compound in corresponding concentrations (used for screening: $10^{-5}$, $10^{-7}$, $10^{-9}$M) was added in sequence.

5) To all of the tubes, 40 µl [$^3$H]-8-OH-DPAT (7.34 nM) was added in sequence, and the final concentration of the labeled ligand was 1.28 nM.

6) Tris-HCl buffer solution (50 mM Tris-HCl, 1 mM EDTA, 5 mM MgCl$_2$, 0.1 mM PMSF, 0.1% NaN$_3$, pH 7.4) was supplied to all of the tubes to reach a volume of 300 µl. The positive control drug used were 5-HT and 8-OH-DPAT.

7) The reaction was performed at 25° C. for 1 h.

8) Then samples were applied to 49-type glass fibre filter, vacuum suction filtered, then washed three times with 2 ml ice-cold Tris-HCl buffer solution (50 mM Tris-HCl buffer solution, 1 mM EDTA, 5 mM MgCl$_2$, 1 mM PMSF, 0.1% NaN$_3$, 3 µg/ml proteinase inhibitor, pH 7.4). The filter was dried and placed in a scintillation vial with 1 ml of scintillation fluid. The radio-activity was measured by a scintillation counter.

The test of competitive binding for the compound and SERT (using [$^3$H]-citalopram for competition) was performed by the same above steps, wherein the non-specific binding ligand in the reaction was fluoxetine in a concentration of 50 µM, the concentration of the labeled ligand [$^3$H]-citalopram was 1 nM. The positive control drugs used were duloxetine and fluoxetine.

1.4.2 Binding Test of YL-0911 for SERT and NET (1) Establishment of Human Embryonic Kidney 293 Cells Stably Expressing for the Human SERT or NET 1) Amplification, Extraction and Identification of Plasmid Preparation of LB liquid culture medium: used for amplification of competent bacteria Amplification of SERT and NET recombinant plasmid: the competence of JM109 bacteria was prepared, the bacteria were transformed, and the transformed bacteria was amplified in a large amount.

Extraction, purification and identification of recombinant plasmid: enzymatic digestion of recombinant plasmid, identification of agarose gel electrophoresis, extraction of recombinant plasmid in large amount and purification, measurement of plasmid sequence, confirmation of the correct sequence of plasmid.

2) Cell Culture and Stable Transfection

Stable transfection was performed according to Lipofectamine 2000 method to prepare single cell cloned cell line.

1.4.3 Radioligand Binding Test of YL-0911 for SERT or 5-HT$_{1A}$ Receptor and Saturation Binding Text of [$^3$H]-Citalopram for SERT or [$^3$H]-8-OH-DPAT for 5-HT$_{1A}$ (1) Preparation Membrane Protein from Cell Lines of Stably Expression SERT The membrane protein extraction kit purchased from Applygen Company was used for extraction, and the steps and conditions thereof were performed according to the specification.

(2) Measurement of Protein Content

Protein measurement by Lowrry method: the concentrations of SERT and NET protein extracted from the cells were separately measured as 4.3 mg/ml, 3.9 mg/ml, and the content of 5-HT$_{1A}$ receptor extracted from rat hippocampi was 5.5 mg/ml.

(3) Saturation Binding Test of [$^3$H]-8-OH-DPAT and 5-HT$_{1A}$ Receptor, [$^3$H]-Citalopram and SERT 1) To all tubes, 5-HT$_{1A}$ receptor protein extracted from rat hippocampi tissue in an amount of 50 µg was added in sequence.

2) To the nonspecific binding tubes, 50 µl of non-labeled ligand way100635 was added, and the final concentration of the non-labeled ligand was 10 µM, and a pre-reaction was performed for 15 min.

3) Various concentrations of [$^3$H]-DPAT (0.2 nM, 0.3 nM, 0.6 nM, 0.9 nM, 1.2 nM, 1.5 nM, 2.4 nM, 4.0 nM, 5.5 nM) was added to different tubes.

4) Tris-HCl buffer (pH 7.4) was supplied to all reaction tubes to reach a volume of 200 µl.

5) The reaction was performed at 37° C. for 1 h.

6) The samples were then applied to 49-type glass fibre filters, vacuum suction filtered, washed 5 times with 5 ml ice-cooled Tris-HCl buffer. The filter was dried and placed in a scintillation vial with 1 ml of scintillation fluid. The radioactive intensity was measured by using LS6500 type liquid scintillation counter.

The saturation binding test of SERT and [$^3$H]-citalopram was performed by the same above steps, wherein each of the tubes was added in sequence with SERT protein extracted from the transfected cells in an amount of 15 µg, the non-labeled ligand was fluoxetine with a concentration of 100 µM; the labeled ligand [$^3$H]-citalopram had a concentration of (0.4 nM, 0.6 nM, 0.9 nM, 1.2 nM, 1.5 nM, 2.4 nM, 3.6 nM, 7.2 nM, 8.2 nM, 9.2 nM, 10.2 nM).

(4) Competitive Binding Test of YL-0911 and 5-HT$_{1A}$ Receptor

1) Test tubes were placed in 37° C. reactor.
2) To all tubes, receptor protein in an amount of 50 µg was added in sequence.
3) To the test tubes, 20 µl of the drug to be tested (selecting a concentration ranging from $10^{-3}$-$10^{-10}$M) was added.
4) To the non-specific binding tubes, 50 µl of non-labeled ligand WAY100635 was added, and the final concentration of the non-labeled ligand was 10 µM, and a pre-reaction was performed for 15 min.
5) To all test tubes, 60 µl of labeled ligand was added in sequence, and the labeled ligand had a final concentration of 0.25 nM.
6) Tris-HCl (pH 7.4) was supplied to all of the reaction tubes to reach a volume of 200 µl.
7) The reaction was performed at 37° C. for 1 h.
8) The samples were then applied to 49-type glass fibre filters, vacuum suction filtered, washed 5 times with 5 ml ice-cooled Tris-HCl buffer. The filter was dried and placed in a scintillation vial with 1 ml of scintillation fluid. The radioactive intensity was measured by using LS6500 type liquid scintillation counter.

The competitive binding test of SERT and [$^3$H]-citalopram was performed by the same above steps, wherein the content of the protein extracted from cells and added to SERT was 15 µg, the non-labeled ligand was fluoxetine, and the concentration of the labeled ligand was 1.4 nM.

1.4.4 Test of 5-HT Reuptake Inhibition of YL-0911 and its Positive Drug in Rat Synaptosome (1) Preparation of Synaptosome Protein.
1) Rats were rapidly decapitated and the brains were removed, and hippocampi and cortex were separated on ice.
2) Same brain tissues of 3 rats were combined, to which 10 times volume of ice-bath homogenate was added, and homogenized.
3) The homogenate was centrifuged at 4° C. under 1500 g for 10 minutes and the precipitate was decanted.
4) The supernatant was centrifuged at 4° C. under 12000 g for 15 minutes and the supernatant was decanted, and the precipitate portion was a crudely produced synaptosome.
5) Washed with resuspension buffer twice and centrifuged at 4° C. under 13000 g for 10 minutes and resuspended again.
6) Protein concentration was measured by Lowrry method.
7) The synaptosome was preserved on ice, and the test was completed within 4-6 h.

Note: The whole procedure for the preparation of synaptosome was performed at a low temperature.

(2) Measurement of Protein Content:
Protein was measured by Lowrry method: the measured concentration of the crudely produced synaptosome was 8.4 mg/ml.

(3) Test of 5-HT Reuptake Inhibition of YL-0911 and its Positive Drugs in rat Synaptosome 1) To all tubes, the crudely produced synaptosome protein was added in an amount of 50 µg in sequence.
2) To nonspecific binding tubes, 50 µl of fluoxetine was added, and the final concentration thereof was 100 µM, and a pre-reaction was performed for 15 minutes.
3) To the test tubes, the drug to be tested in various concentrations in range of $10^{-3}$-$10^{-10}$M was added in sequence and reacted for 15 minutes.
4) To all of the test tubes, 30 µl labeled ligand [$^3$H]-5-HT was added in sequence, and the final concentration of the labeled ligand was 20.3 nM.
5) Tris-HCl (pH 7.4) was supplied to all reaction tubes to reach a volume of 200 µl.
6) The reaction was performed at 37° C. for 10 minutes.
7) The samples were then applied to 49-type glass fibre filters, vacuum suction filtered, washed 5 times with 10 ml ice-cooled Tris-HCl buffer. The filter was dried and placed in a scintillation vial with 1 ml of scintillation fluid. The radioactive intensity was measured by using LS6500 type liquid scintillation counter.

(4) Preliminary Test of NET Binding Effect of YL-0911 and Positive Control Drugs Two different drug concentrations, $10^{-5}$ and $10^{-7}$ mol/L, were used to determine the binding effect of YL-0911 on NET protein extracted from the HEK-293 cell lines of stably expression NET.

1.4.5 Statistical Method $$\text{Inhibition percent } (\%) = \frac{\text{total binding } CPM \text{ number} - \text{dosing tube } CPM \text{ number}}{\text{total binding } CPM \text{ number} - \text{non-specific } CPM \text{ number}} \times 100\%$$

The calculated inhibition percents were used to calculate IC$_{50}$ value by using Orgin7.0/GraphPad Prism 4.0 software. The results of saturation test were used to calculate K$_d$ value by using Orgin7.0/GraphPad Prism 4.0 software.

IC$_{50}$ and K$_d$ were used to calculate Ki value. K$_i$=(IC$_{50}$/(1+[L]/K$_a$), [L] is the concentration of the added radioligand.

1.4.6 Research Results 1.4.6.1 Experimental Screening of Binding of YL Series Compounds to SERT and 5-HT$_{1A}$ (1) The Results of the Competitive Binding Test of YL Series Compound to 5-HT$_{1A}$ Receptor are Shown in Table 1.

TABLE 1

Results of the competitive binding test of YL series compound to 5-HT$_{1A}$ receptor

| Compound | Inhibition percent (I %) | |
|---|---|---|
| | $10^{-5}$(mol/L) | $10^{-7}$(mol/L) |
| Compound 1 (YL-0911) | 100 | 85 |
| Compound 2 | 100 | 58 |
| Compound 3 | 100 | 10 |
| Compound 4 | 100 | 57 |
| Compound 5 | 94 | 62 |
| Compound 6 | 100 | 74 |
| Compound 7 | 59 | 2 |
| Compound 8 | 42 | 19 |
| Compound 9 | 100 | 25 |
| Compound 10 | 76 | 37 |
| Compound 11 | 57 | 14 |

TABLE 1-continued

Results of the competitive binding test of YL series compound to 5-$HT_{1A}$ receptor

| Compound | Inhibition percent (I %) | |
|---|---|---|
| | $10^{-5}$(mol/L) | $10^{-7}$(mol/L) |
| Compound 12 | 61 | 30 |
| 8-OH-DAPT | 100 | 85 |

The results show that, in comparison with the positive control drug at different concentrations, the compounds of the present invention have essentially comparative affinity to 5-$HT_{1A}$.

(2) Results of Competitive Binding Test of Compounds to 5-HT Transport Protein (SERT)

According to the results in Table 1, the inventors further examined 5 compounds obtained in Example 1, 2, 4, 5 and 6 as preferable compounds of the present invention, so as to observe their affinity to SERT. The results are shown in Table 2.

TABLE 2

Results of competitive binding test of compounds to 5-HT transport protein (SERT)

| Compound | Inhibition percent (I %) | |
|---|---|---|
| | $10^{-5}$ (mol/L) | $10^{-7}$ (mol/L) |
| Compound 1 (YL-0911) | 100 | 84 |
| Compound 2 | 100 | 50 |
| Compound 4 | 100 | 58 |
| Compound 5 | 100 | 77 |
| Compound 6 | 87 | 44 |
| Fluoxetine | 100 | 77 |
| Duloxetine | 100 | 65 |

The results show that, in comparison with positive control drugs at different concentrations, the compounds of the present invention, in particular Compounds 1, 4 and 5, have essentially comparative affinity to SERT.

In order to further observe the biological activity of the compounds of the present invention, the illustrative Compound 1 (YL-0911) was further tested as follows.

1.4.6.2 Saturation Binding Test of 5-$HT_{1A}$ Receptor (Extracted from Hippocampi) and SERT (Transport Protein hSERT Extracted from Transfected Cell Lines)

The research results show that the test $K_d$ value as calculated from the saturation binding of [$^3$H]-citalopram to SERT was 1.50±0.6 nM, which was consistent with that reported in literatures. The test $K_d$ value as calculated from the saturation binding of [$^3$H]-8-OH-DPAT to 5-$HT_{1A}$ was 0.96±0.38 nM, which was essentially consistent with that reported in literatures. The above saturation curves are not show in detail.

1.4.6.3 Competitive Binding Test of YL-0911 and Positive Drugs, Buspirone, 8-OH-DPAT, to 5-$HT_{1A}$ Receptor (the Results are Shown in FIG. 1)

The results show that YL-0911 has a high affinity for 5-$HT_{1A}$ with the K, value of 0.44±0.32 nM.

Figure 2:
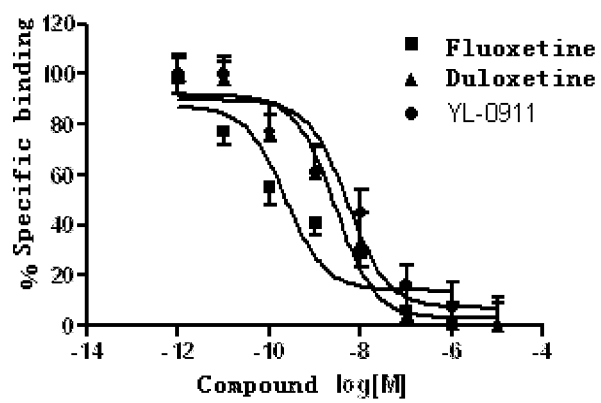
FIG. 2 represents the competitive binding curves of the Example compound 1 (YL-0911) of the present invention and the positive drugs thereof, duloxetine and fluoxetine, to SERT radioligand.

1.4.6.4 Competitive Binding Test of YL-0911 and Positive Drugs, Duloxetine and Fluoxetine, to SERT (the Results are Shown in FIG. 2)

The results show that YL-0911 has a high affinity for SERT with the $K_1$ value of 5.38±0.27 nM.

Figure 3:
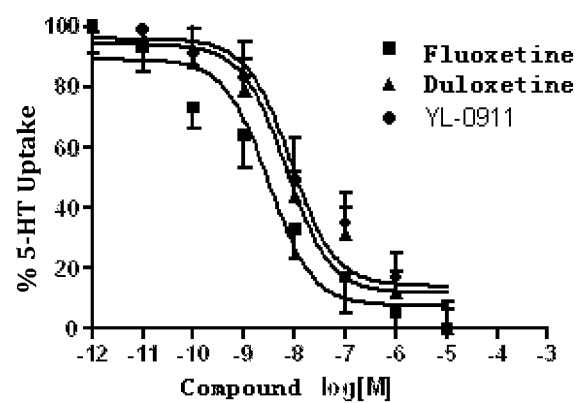
FIG. 3 represents the inhibition curves of the Example compound 1 (YL-0911) of the present invention and the positive drugs thereof to 5-HT reuptake in crudely produced synaptosomes of rat.

1.4.6.5 5-HT Reuptake Inhibition Curves of YL-0911 and Positive Drugs Thereof in Crudely Produced Rat Synaptosomes (the Results are Shown in FIG. 3)

The results show that YL-0911 can significantly inhibit the 5-HT reuptake in rat brain with the $IC_{50}$ of 8.51±0.23 Nm.

Summary of results: according to the $K_d$ value obtained in the saturation test and the $IC_{50}$ value obtained the competitive binding test, $K_i$ was calculated according to the formula; the 5-HT reuptake test was performed by using the synaptosomes extracted from rat cortex, and the results thereof were analyzed to obtain $IC_{50}$. All results are summarized in the following Table 3.

TABLE 3

Activity comparison of YL-0911 with the corresponding positive controls

| Drug | SERT $K_i$ | 5-HT reuptake $IC_{50}$ | 5-$HT_{1A}$ receptor $K_i$ |
|---|---|---|---|
| YL-0911 | 5.38 ± 0.27 nM | 8.51 ± 0.23 nM | 0.44 ± 0.32 nM |
| 8-OH-DPAT | — | — | 0.14 ± 0.34 nM |
| Buspirone | — | — | 1.098 ± 0.25 nM |
| Duloxetine | 2.13 ± 0.58 nM | 6.86 ± 0.28 nM | — |
| Fluoxetine | 0.152 ± 0.32 nM | 3.09 ± 0.32 nM | — |

1.5 Brief Summary (1) It can be seen from the above figures and tables that the illustrative compound YL-0911 of the present invention has affnitiy to SERT very similar to the two positive drugs, $K_i$ value is 5.38±0.27 nM. Its affinity to 5-$HT_{1A}$ is obviously better than that of the positive drug buspirone, $K_i$ value is 0.44±0.32 nM.

(2) In the test of YL-0911 for SERT reuptake inhibition, the $IC_{50}$ value of 5-HT reuptake inhibition is 8.51±0.23 nM.

(3) As for the selectivity of YL-0911 to NET, the affinity to NET is obviously lower than the affinity to SERT and 5-$HT_{1A}$.

In summary, the illustrative compound YL-0911 of the present invention is a compound having high affinity to SERT and 5-$HT_{1A}$, and has relative high inhibition effect on 5-HT reuptake, so that the illustrative compound YL-0911 of the present invention is a novel compound having two target points and potential antidepressant like effect.

Biological effect test 2: Evaluation of the compounds of the present invention in activities of antidepressant, anxiolytic, cognitive enhancing behaviors The illustrative compound YL-0911 of the present invention was used in the test.

2.1 The Despair Models for Antidepressant Behaviors 2.1.1 Forced Swim Test in Mice Forced swim test in mice is an acute behavioral despair model established by Porsolt, et al.

(1) Experimental device: a glass cylinder (diameter 13 cm, height 24 cm, containing 10 cm of water maintained at 25).

(2) Experimental method: Male Kunming mice weighing 20-25 g. The mice were gently put in the water 1 h after intragastrically drug administration, and then the duration of immobility in the last 4 min of total 6 min test was recorded.

(3) Experimental results: see Table 4.

TABLE 4

Effect of acute intragastrical administration of YL-0911 on the immobility time in the forced swim test in mice (x ± s, n = 10)

| Drug | Dose (mg/kg) | Administration route | Immobility time (s) |
|---|---|---|---|
| Vehicle | — | p.o. | 150.7 ± 57.7 |
| Imipramine | 40 | p.o. | 88.0 ± 58.2** |
| YL-0911 | 0.625 | p.o. | 126.1 ± 60.9 |
| | 1.25 | p.o. | 72.0 ± 46.5** |
| | 2.5 | p.o. | 135.7 ± 42.6 |
| | 5 | p.o. | 149.6 ± 39.1 |

**P < 0.01, compared with the vehicle.

It can be seen from the table that the intagastrically administered illustrative compound YL-0911 of the present invention exhibits antidepressant-like effect in the forced swim test in mice.

2.1.2 Tail Suspension Test in Mice

Tail suspension test in mice is an acute behavioral despair model established by Stem, et al. (1985).

1) Experimental device: an experimental frame with spacing boards which dividing the experimental frame into 2 experimental chambers (20×25×30 cm). A clamp is mounted on a through cross rod in the chamber for clamping mice tail so as to suspend the mice.

2) Experimental method: Male Kunming mice weighing 20-25 g. The mice were intragastrically administered with YL-0911 or vehicle (distilled water). After 1 h, wrap adhesive tape around the mouse's tail in position three quarters of the distance from the base of the tail and then suspend the animals by passing the suspension hook through the adhesive tape 5 cm above the table. The duration of immobility in the last 4 min of total 6 min test was recorded.

3) Experimental results: see Table 5.

TABLE 5

Effect of acute intragastrical administration of YL-0911 on the immobility time in the tail suspension test in mice ($\bar{x} \pm s$, n = 10)

| Drug | Dose (mg/kg) | Administration route | Immobility time (s) |
|---|---|---|---|
| Vehicle | — | p.o. | 137.3 ± 44.2 |
| Fluoxetine | 30 | p.o. | 56.2 ± 41.7*** |
| YL-0911 | 0.625 | p.o. | 105.4 ± 24.6 |
|  | 1.25 | p.o. | 93.8 ± 38.7* |
|  | 2.5 | p.o. | 71.0 ± 39.1** |
|  | 5 | p.o. | 98.8 ± 45.3* |

*$P < 0.05$,
**$P < 0.01$,
***$P < 0.001$, compared with the vehicle.

It can be seen from the table that the intagastrically administered illustrative compound YL-0911 of the present invention exhibits antidepressant-like effect in the tail suspension test in mice.

2.2 Animal Model of Anxiolytic Behaviors

Hole board test, an animal model of anxiety established by Boissie, et al (1962), was performed in mice.

1) Experimental device: a transparent Perspex box (40×40×27 cm) which had four holes (3 cm in diameter, 1.8 cm in depth) in the floor. The distance of each hole center to its closest wall is 10 cm.

2) Experimental method: Male Kunming mice weighing 20-25 g. The mice were intragastrically administered with YL-0911 or vehicle (distilled water). After 23 days, the mice were placed at center of the hole board with their backs facing to the observer. A head dip was scored if the animal's head dipped into the hole at least up to eye level The latency to the first head-dip, the number of head-dips and the time spent in head-dipping were recorded for 5 min.

3) Experimental results: see Table 6.

TABLE 6

Effects of long-term intragastrically administered YL-0911 on hole board test in mice ($\bar{x} \pm s$, n = 10)

| Drug | Dose (mg/kg) | Administration route | the latency to the first head-dip (s) | Number of Head dips | Time of head dipping (s) |
|---|---|---|---|---|---|
| Vehicle | — | p.o. | 107.5 ± 17.38 | 3.40 ± 0.58 | 3.14 ± 0.81 |
| Fluoxetine | 10 | p.o. | 42.70 ± 9.43*** | 9.60 ± 1.49** | 6.31 ± 1.03* |
| YL-0911 | 0.625 | p.o. | 62.60 ± 16.75** | 6.40 ± 0.97 | 3.75 ± 0.91 |
|  | 1.25 | p.o. | 33.00 ± 6.34*** | 10.60 ± 1.17*** | 6.86 ± 0.55* |
|  | 2.5 | p.o. | 35.20 ± 8.12*** | 11.00 ± 1.24*** | 8.09 ± 0.58** |
|  | 5 | p.o. | 31.60 ± 6.88*** | 7.40 ± 1.00* | 5.95 ± 0.93* |

*$P < 0.05$,
**$P < 0.01$,
***$P < 0.001$, compared with the vehicle.

It can be seen from the results in the table that the long-term treatment with illustrative compound YL-0911 of the present invention exhibits anxiolytic-like effects in the hole board test in mice.

2.3 Cognition-Enhancing Behaviors in Animal Models.

Novel object recognition test is a cognitive behavior model established by Lima, et al.

1) Experimental device: a white Perspex box (60×60×16 cm), two completely identical objects, and one completely different object.

2) Experimental method: Male Kunming mice weighing 20-25 g. The mice were intragastrically administered with YL-0911 or vehicle (distilled water) for 5 days. On day 6, after treatment with YL-0911 or vehicle, each mouse was placed into the Perspex box at the same place for 5 min as habituation. On day 7, the mice were administered YL-0911 or vehicle and then individually placed in the Perspex box at the same place containing two identical objects located in the two diagonal corners for 5 minutes. On day 8, mice were tested for memory using the same procedure as day 7 except that one of the familiar objects was replaced with a novel object.

3) Experimental results: see Table 7

TABLE 7

Effects of intragastrically administered YL-0911 on novel object recognition test ($\bar{x} \pm s$, n = 10)

| Drug | Dose (mg/kg) | Administration route | Recognition index |
|---|---|---|---|
| Vehicle | — | p.o. | 38.22 ± 4.48 |
| YL-0911 | 0.625 | p.o. | 59.95 ± 2.74** |
|  | 1.25 | p.o. | 64.76 ± 5.02*** |
|  | 2.5 | p.o. | 63.78 ± 3.10*** |

*$P < 0.05$,
**$P < 0.01$,
***$P < 0.001$, compared with the vehicle.

It can be seen from the results in the table that the long-term treatment with illustrative compound YL-0911 of the present invention exhibits enhancing cognition activity in the novel object recognition test of mice.

Although the specific embodiments of the present invention have been described in details, those skilled in the art would understand, according to the disclosed teachings, these details could be modified and changed, and all of these changes fall within the protection scope of the present invention. The protection scope of the present invention is given by the attached claims and any equivalents thereof.

The invention claimed is:

1. A compound of Formula I, a tautomer thereof, a racemate or optical isomer thereof, or a pharmaceutically acceptable salt or a solvate thereof,

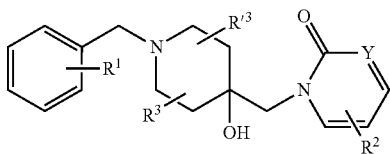

wherein:
$R^1$, $R^2$ are H, halogen (F, Cl, Br, I), alkyl, substituted hydrocarbyl, alkenyl, substituted alkenyl, $C_1$-$C_6$ alkoxy, $C_1$-$C_6$ alkylamino, di-($C_1$-$C_6$ alkyl)amino, $C_{1-10}$ hydrocarbylacyloxy, $C_{1-10}$ hydrocarbylamido, carboxy, $C_{1-10}$ hydrocarbyloxyformyl, carbamoyl, or $C_{1-10}$ hydrocarbylaminoformyl, the substituent of each substituted group is selected from the group consisting of halogen, hydroxy, cyano, nitro, $C_{1-6}$ alkyl, $C_{1-6}$ alkoxy, $C_{1-6}$ alkylthio, mono-, di- or tri-halogenated $C_{1-6}$ alkyl, amino, $C_{1-6}$ alkylamino, $C_{1-10}$ hydrocarbylacyloxy, or $C_{1-10}$ hydrocarbylamido;

$R^1$, $R^2$ can be same or different, wherein $R^1$ can represent 1-3 substituents which can be at o-, m- or p-position of benzene ring; $R^2$ can represent 1-3 substituents;

$R^3$, $R'^3$ independently are H, alkyl, substituted hydrocarbyl, alkenyl, substituted alkenyl, $C_1$-$C_6$ alkoxy, $C_1$-$C_6$ alkylamino, di-($C_1$-$C_6$ alkyl)amino, $C_{1-10}$ hydrocarbylacyloxy, $C_{1-10}$ hydrocarbylamido, $C_{1-10}$ hydrocarbyloxyformyl, carbamoyl, or $C_{1-10}$ hydrocarbylaminoformyl, the substituent of each substituted group is selected from the group consisting of halogen, hydroxy, cyano, nitro, $C_{1-6}$ alkyl, $C_{1-6}$ alkoxy, $C_{1-6}$ alkylthio, mono-, di- or tri-halogenated $C_{1-6}$ alkyl, amino, $C_{1-6}$ alkylamino, $C_{1-10}$ hydrocarbylacyloxy, or $C_{1-10}$ hydrocarbylamido;

Y is CH or N; wherein $R^2$ represents at most 3 substituents which can be at 3-, 4-, 5- or 6-position when Y is CH; and wherein $R^2$ represents at most 2 substituents which can be at 4-, 5- or 6-position of heterocyclic ring of heterocyclic ring when Y is N.

2. The compound of claim 1, a tautomer thereof, a racemate or optical isomer thereof, or a pharmaceutically acceptable salt or a solvate thereof, wherein $R^1$, $R^2$, $R^3$, $R'^3$ each independently is H, halogen (F, Cl, Br, I), $C_1$-$C_6$ alkyl, substituted $C_1$-$C_6$ alkyl, $C_1$-$C_6$ alkenyl, substituted $C_1$-$C_6$ alkenyl, $C_1$-$C_6$ alkoxy, $C_1$-$C_6$ alkylamino, di-($C_1$-$C_6$ alkyl)amino, $C_{1-10}$ hydrocarbylacyloxy, $C_{1-10}$ hydrocarbylamido, carboxy, $C_{1-10}$ hydrocarbyloxyformyl, carbamoyl, or $C_{1-10}$ hydrocarbylaminoformyl, the substituent of each substituted group is selected from the group consisting of halogen, hydroxy, cyano, nitro, $C_{1-6}$ alkyl, $C_{1-6}$ alkoxy, $C_{1-6}$ alkylthio, mono-, di- or tri-halogenated $C_{1-6}$ alkyl, amino, $C_{1-6}$ alkylamino, $C_{1-10}$ hydrocarbylacyloxy, or $C_{1-10}$ hydrocarbylamido; wherein $R^1$ can represent 1-3 substituents which can be at o-, m- or p-position of benzene ring; $R^2$ can represent 1-3 substituents; wherein $R^2$ represents at most 3 substituents which can be at 3-, 4-, 5- or 6-position when Y is CH; and wherein $R^2$ represents at most 2 substituents which can be at 4-, 5- or 6-position of heterocyclic ring of heterocyclic ring when Y is N.

3. The compound of claim 1, a tautomer thereof, a racemate or optical isomer thereof, or a pharmaceutically acceptable salt or a solvate thereof, wherein $R^1$, $R^2$, $R^3$, $R'^3$ each independently is H, halogen (F, Cl, Br, I), $C_1$-$C_6$ alkyl, substituted $C_1$-$C_6$ alkyl, or $C_1$-$C_6$ alkoxy; the substituent of each substituted group is selected from the group consisting of halogen, hydroxy, cyano, nitro, $C_{1-6}$ alkyl, $C_{1-6}$ alkoxy, $C_{1-6}$ alkylthio, mono-, di- or tri-halogenated $C_{1-6}$ alkyl, amino, $C_{1-6}$ alkylamino, $C_{1-10}$ hydrocarbylacyloxy, or $C_{1-10}$ hydrocarbylamido.

4. The compound of claim 1, a tautomer thereof, a racemate or optical isomer thereof, or a pharmaceutically acceptable salt or a solvate thereof, wherein $R^1$, $R^2$, $R^3$, $R'^3$ each independently is H, F, Cl, Br, $C_1$-$C_4$ alkyl, or $C_1$-$C_4$ alkoxy.

5. The compound of claim 1, a tautomer thereof, a racemate or optical isomer thereof, or a pharmaceutically acceptable salt or a solvate thereof, wherein $R^1$, $R^2$, $R^3$, $R'^3$ each independently is H, F, Cl, Br, methyl, ethyl, methoxyethyl, methoxy, or ethoxy.

6. The compound of claim 1, a tautomer thereof, a racemate or optical isomer thereof, or a pharmaceutically acceptable salt or a solvate thereof, wherein:
Y is CH.

7. The compound of claim 1, or a tautomer thereof, racemate thereof, optical isomer thereof, or pharmaceutically acceptable salt or a solvate thereof,

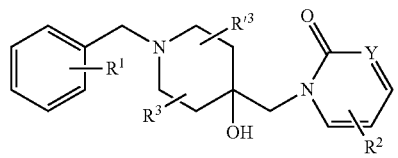

wherein:
$R^1$ represents H or represents 1-3 substituents selected from halogen;
$R^2$ represents H or represents 1-3 substituents selected from halogen, and $C_{1-6}$ alkyl;
$R^3$ and $R'^3$ each are H;
Y is CH.

8. The compound of claim 1, a tautomer thereof, a racemate or optical isomer thereof, or a pharmaceutically acceptable salt or a solvate thereof, wherein:
(1) $R^1$ represents H, 2-F, 4-F, 2,3-difluoro, 2,4-difluoro, 2,5-fluoro or 2,6-difluoro;
(2) $R^2$ is H, Br, methyl, or methoxy; or
(3) $R^3$, $R'^3$ each independently is H, methyl or methoxy.

9. The compound of claim 1, a tautomer thereof, a racemate or optical isomer thereof, or a pharmaceutically acceptable salt or a solvate thereof, which is selected from the group consisting of:
  1-[(1-benzyl-4-hydroxypiperidin-4-yl)-methyl]-pyridin-2 (1H)-one;
  1-{[1-(2-fluorobenzyl)-4-hydroxypiperidin-4-yl]-methyl}-pyridin-2(1H)-one;
  1-{[1-(4-fluorobenzyl)-4-hydroxypiperidin-4-yl]-methyl}-pyridin-2(1H)-one;
  1-{[1-(2,4-difluorobenzyl)-4-hydroxypiperidin-4-yl]-methyl}-pyridin-2(1H)-one;
  5-bromo-1-[(1-benzyl-4-hydroxypiperidin-4-yl)-methyl]-pyridin-2(1H)-one;

5-bromo-1-{[1-(2-fluorobenzyl)-4-hydroxypiperidin-4-yl]-methyl}-pyridin-2(1H)-one;
5-bromo-1-{[1-(4-fluorobenzyl)-4-hydroxypiperidin-4-yl]-methyl}-pyridin-2(1H)-one;
5-bromo-1-{[1-(2,4-difluorobenzyl)-4-hydroxypiperidin-4-yl]-methyl}-pyridin-2(1H)-one;
4-methyl-1-[(1-benzyl-4-hydroxypiperidin-4-thyl]-pyridin-2(1H)-one;
4-methyl-1-{[1-(2-fluorobenzyl)-4-hydroxypiperidin-4-yl]-methyl}-pyridin-2(1H)-one;
4-methyl-1-{[1-(4-fluorobenzyl)-4-hydroxypiperidin-4-yl]-methyl}-pyridin-2(1H)-one;
4-methyl-1-{[1-(2,4-difluorobenzyl)-4-hydroxypiperidin-4-yl]-methyl}-pyridin-2(1H)-one;
and a tautomer thereof, a racemate or optical isomer thereof, a pharmaceutically acceptable salt or a solvate thereof.

10. A pharmaceutical composition, comprising the compound of claim 1, a tautomer thereof, a racemate or optical isomer thereof, or a pharmaceutically acceptable salt or a solvate thereof, and a pharmaceutically acceptable carrier or excipient.

11. A method for the treatment of one or more nervous system diseases associated with 5-HT system dysfunction, the one or more nervous system diseases chosen from the group of depression and anxiety, in a patient in need of treatment, comprising administrating a therapeutically effective amount of the compound of claim 1, a tautomer thereof, a racemate or optical isomer thereof, or a pharmaceutically acceptable salt or a solvate thereof, to the patient.

12. A method for preparing the compound of Formula I according to claim 1, a tatomer thereof, a racemate or optical isomer thereof, or a pharmaceutically acceptable salt or a solvate thereof, which comprises the following steps:
a) treating a ketone compound of Formula II with Me$_3$SI or Me$_3$SOI in the presence of a base to afford an epoxy compound of Formula IIa:

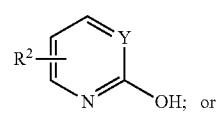

II

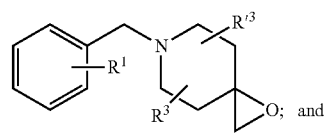

IIa b) treating the epoxy compound of Formula IIa with a hydroxy compound of Formula III under heating to afford the compound of Formula I, a tautomer thereof, a racemate or optical isomer thereof, or a pharmaceutically acceptable salt or a solvate thereof:

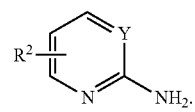

III treating the epoxy compound of Formula IIa with an amine compound of Formula III' under heating to afford the compound of Formula I, a tautomer thereof, a racemate or optical isomer thereof, or a pharmaceutically acceptable salt or a solvate thereof:

III'

13. The compound of claim 1, a tautomer thereof, a racemate or optical isomer thereof, or a pharmaceutically acceptable salt or a solvate thereof, wherein R$^1$, R$^2$, R$^3$, R$^{'3}$ each independently is H, F, Cl, Br, I, C$_1$-C$_6$ alkyl, C$_1$-C$_3$ alkoxyethyl, or C$_1$-C$_6$ alkoxy.

14. The compound of claim 1, a tautomer thereof, a racemate or optical isomer thereof, or a pharmaceutically acceptable salt or a solvate thereof, wherein:
Y is N.

* * * * *